(12) United States Patent
Manley et al.

(10) Patent No.: US 6,881,736 B1
(45) Date of Patent: Apr. 19, 2005

(54) VITRONECTIN RECEPTOR ANTAGONISTS

(75) Inventors: Peter J. Manley, Harleysville, PA (US); William H. Miller, Collegeville, PA (US); Irene N. Uzinskas, Villanova, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 48 days.

(21) Appl. No.: 10/070,057

(22) PCT Filed: Sep. 7, 2000

(86) PCT No.: PCT/US00/24514
§ 371 (c)(1),
(2), (4) Date: Feb. 28, 2002

(87) PCT Pub. No.: WO01/17959
PCT Pub. Date: Mar. 15, 2001

Related U.S. Application Data
(60) Provisional application No. 60/152,780, filed on Sep. 7, 1999.

(51) Int. Cl.[7] .................... A61K 31/44; A61K 31/4427; A61K 31/444; C07D 417/08; C07D 413/08
(52) U.S. Cl. .................... 514/235.8; 514/352; 514/340; 514/300; 514/335; 544/124; 546/312; 546/271.4; 546/269.7; 546/122; 546/261
(58) Field of Search .............................. 546/312, 271.4, 546/269.7, 122, 261; 514/352, 340, 235.8, 300, 335; 544/124

(56) References Cited

U.S. PATENT DOCUMENTS
2002/0147334 A1 * 10/2002 Miller et al. ................ 540/553

FOREIGN PATENT DOCUMENTS
WO WO 99/15508 4/1999
WO WO 99/45927 9/1999

OTHER PUBLICATIONS
Takeno, et al., "Preparation of substituted 3-phenylpropionic . . . ," *Chem Abst.* 126: Abst. 117964, (1997).
Takeno, et al., "Preparation of (oxazolyl) . . . ," *Chem Abst.* 126:Abst. 89361, (1997).
Miller, et al., "Preparation of pyridinylethoxyphenybutanoates . . . " *Chem Abst.* 131:Abst. 124194, (1999).

* cited by examiner

*Primary Examiner*—Patricia L. Morris
(74) *Attorney, Agent, or Firm*—Grace C. Hsu; Mary E. McCarthy; Charles M. Kinzig

(57) ABSTRACT

Compounds of the formula (I) are disclosed which are vitronectin receptor antagonists and are useful in the treatment of osteoporosis:

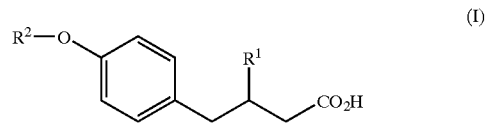

wherein
$R^1$ is Het or Ar
$R^2$ is

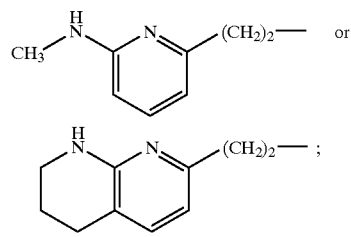

or a pharmaceutically acceptable salt thereof.

6 Claims, No Drawings

VITRONECTIN RECEPTOR ANTAGONISTS

The application claims the benefit of 60/152,780 filed on Sep. 7, 1999.

FIELD OF THE INVENTION

This invention relates to pharmaceutically active compounds which inhibit the vitronectin receptor and are useful for the treatment of inflammation, cancer and cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembrane glycoproteins expressed on a variety of cells. These cell surface adhesion receptors include gpIIb/IIIa (the fibrinogen receptor) and $\alpha_v\beta_3$ (the vitronectin receptor). The fibrinogen receptor gpIIb/IIIa is expressed on the platelet surface, and mediates platelet aggregation and the formation of a hemostatic clot at the site of a bleeding wound. Philips, et al, *Blood.,* 1988, 71, 831. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the adhesion of osteoclasts to the bone matrix, a key step in the bone resorption process. Ross, et al. *J. Biol. Chem,* 1987, 262, 7703. A disease characterized by excessive bone resorption is osteoporosis. The $\alpha_v\beta_3$ receptor expressed on human aortic smooth muscle cells mediates their migration into neointima, a process which can lead to restenosis after percutaneous coronary angioplasty. Brown, et al., *Cardiovascular Res.,* 1994, 28, 1815. Additionally, Brooks, et al., *Cell,* 1994, 79, 1157 has shown that an $\alpha_v\beta_3$ antagonist is able to promote tumor regression by inducing apoptosis of angiogenic blood vessels. Thus, agents that block the vitronectin receptor would be useful in treating diseases, such as osteoporosis, restenosis and cancer.

The vitronectin receptor is now known to refer to three different integrins, designated $\alpha_v\beta_1$, $\alpha_v\beta_3$ and $\alpha_v\beta_5$. Horton, et al., *Int. J. Exp. Pathol.,* 1990, 71, 741. $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteopontin and bone sialoprotein I. $\alpha_v\beta_5$ binds vitronectin. The vitronectin receptor $\alpha_v\beta_5$ has been shown to be involved in cell adhesion of a variety of cell types, including microvascular endothelial cells, (Davis, et al., *J. Cell. Biol.,* 1993, 51, 206), and its role in angiogenesis has been confirmed. Brooks, et al., *Science,* 1994, 264, 569. This integrin is expressed on blood vessels in human wound granulation tissue, but not in normal skin.

The vitronectin receptor is known to bind to bone matrix proteins which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 discloses that echistatin, a snake venom peptide which contains the RGD sequence, is a potent inhibitor of bone resorption in tissue culture, and inhibits attachment of osteoclasts to bone.

It has now been discovered that certain compounds are potent inhibitors of the $\alpha_v\beta_3$ and $\alpha_v\beta_5$ receptors. In particular, it has been discovered that such compounds are more potent inhibitors of the vitronectin receptor than the fibrinogen receptor.

SUMMARY OF THE INVENTION

This invention comprises compounds of the formula (I) as described hereinafter, which have pharmacological activity for the inhibition of the vitronection receptor and are useful in the treatment of inflammation, cancer and cardiovascular disorders, such as atherosclerosis and restenosis, and diseases wherein bone resorption is a factor, such as osteoporosis.

This invention is also a pharmaceutical composition comprising a compound according to formula (I) and a pharmaceutically carrier.

This invention is also a method of treating diseases which are mediated by the vitronectin receptor. In a particular aspect, the compounds of this invention are useful for treating atherosclerosis, restenosis, inflammation, cancer and diseases wherein bone resorption is a factor, such as osteoporosis.

DETAILED DESCRIPTION

This invention comprises novel compounds which are more potent inhibitors of the vitronectin receptor than the fibrinogen receptor. This invention comprises compounds of formula (I):

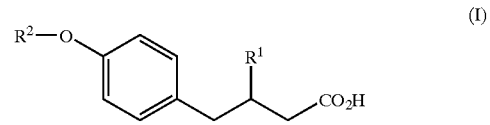

wherein:

$R^1$ is Het- or Ar;

$R^2$ is

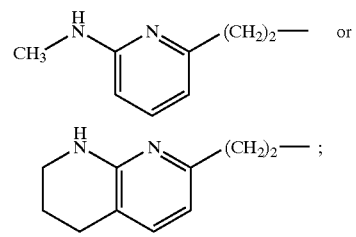

or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique nonracemic compound which may be synthesized and resolved by conventional techniques. According to the present invention, the (S) configuration of the formula (I) compounds is preferred.

In cases in which compounds have unsaturated carbon—carbon double bonds, both the cis (Z) and trans (E) isomers are within the scope of this invention. In cases wherein compounds may exist in tautomeric forms, such as keto-enol tautomers, such as and

and each tautomeric form is contemplated as being included within this invention whether existing in equilibrium or locked in one form by appropriate substitution with R'.

The compounds of formula (I) inhibit the binding of vitronectin and other RGD, containing peptides to the vitronectin receptor. Inhibition of the vitronectin receptor on osteoclasts inhibits osteoclastic bone resorption and is useful in the treatment of diseases wherein bone resorption is associated with pathology, such as osteoporosis and osteoarthritis.

In another aspect, this invention is a method for stimulating bone formation which comprises administering a compound which causes an increase in osteocalcin release. Increased bone production is a clear benefit in disease states wherein there is a deficiency of mineralized bone mass or remodeling of bone is desired, such as fracture healing and the prevention of bone fractures. Diseases and metabolic disorders which result in loss of bone structure would also benefit from such treatment. For instance, hyperparathyroidism, Paget's disease, hypercalcemia of malignancy, osteolytic lesions produced by bone metastasis, bone loss due to immobilization or sex hormone deficiency, Behcet's disease, osteomalacia, hyperostosis and osteopetrosis, could benefit from administering a compound of this invention.

Additionally, since the compounds of the instant invention inhibit vitronectin receptors on a number of different types of cells, said compounds would be useful in the treatment of inflammatory disorders, such as rheumatoid arthritis and psoriasis, and cardiovascular diseases, such as atherosclerosis and restenosis. The compounds of Formula (1) of the present invention may be useful for the treatment or prevention of other diseases including, but not limited to, thromboembolic disorders, asthma, allergies, adult respiratory distress syndrome, graft versus host disease, organ transplant rejection, septic shock, eczema, contact dermatitis, inflammatory bowel disease, and other autoimmune diseases. The compounds of the present invention may also be useful for wound healing.

The compounds of the present invention are also useful for the treatment, including prevention, of angiogenic disorders. The term angiogenic disorders as used herein includes conditions involving abnormal neovascularization. Where the growth of new blood vessels is the cause of, or contributes to, the pathology associated with a disease, inhibition of angiogenisis will reduce the deleterious effects of the disease. An example of such a disease target is diabetic retinopathy. Where the growth of new blood vessels is required to support growth of a deleterious tissue, inhibition of angiogenisis will reduce the blood supply to the tissue and thereby contribute to reduction in tissue mass based on blood supply requirements. Examples include growth of tumors where neovascularization is a continual requirement in order that the tumor grow and the establishment of solid tumor metastases. Thus, the compounds of the present invention inhibit tumor tissue angiogenesis, thereby preventing tumor metastasis and tumor growth.

Thus, according to the methods of the present invention, the inhibition of angiogenesis using the compounds of the present invention can ameliorate the symptoms of the disease, and, in some cases, can cure the disease.

Another therapeutic target for the compounds of the instant invention are eye diseases characterized by neovascularization. Such eye diseases include corneal neovascular disorders, such as corneal transplantation, herpetic keratitis, luetic keratitis, pterygium and neovascular pannus associated with contact lens use. Additional eye diseases also include age-related macular degeneration, presumed ocular histoplasmosis, retinopathy of prematurity and neovascular glaucoma.

This invention further provides a method of inhibiting tumor growth which comprises administering stepwise or in physical combination a compound of formula (I) and an antineoplastic agent, such as topotecan and cisplatin.

With respect to formula (I), suitably $R^1$ is

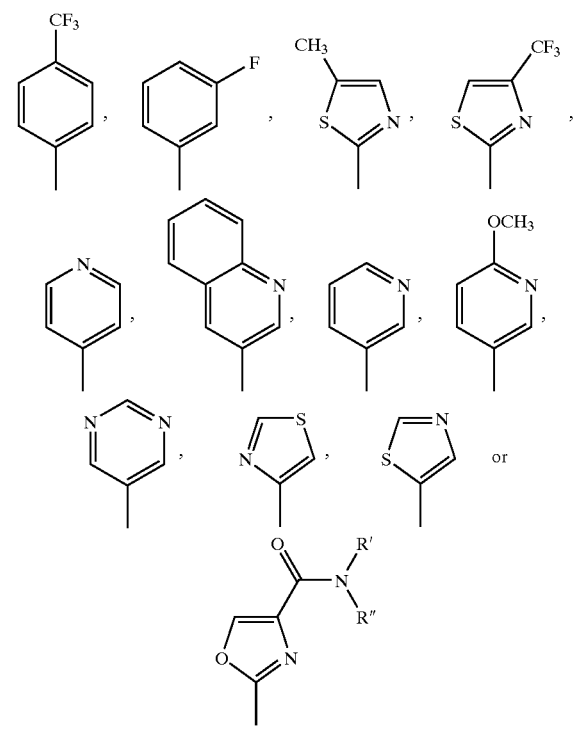

in which R' is $C_{1-4}$alkyl and R" is phenyl, benzyl or —$CH_2CF_3$; or R' and R" are joined to form a morpholinyl ring.

Suitably, $R^2$ is:

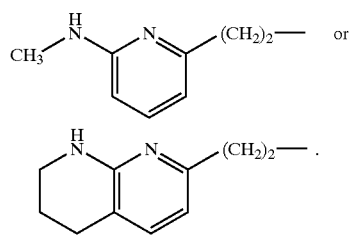

Representative of the novel compounds of this invention are the following:

(±)-4-[4-[2-[6-(methylamino)pyridin-2-yl]-1-ethoxy] phenyl]-3-[4-(trifluoromethyl)phenyl]butanoic acid;

(±)-4[4-[2-[6-(methylamino)pyridin-2-yl]-1-ethoxy]phenyl]-3-[4-[(N-methyl-N-phenylamino)carbonyl]-1,3-oxazol-2-yl]butanoic acid;

(±)-4-[4-[2-[6-(methylamino)pyridin-2-yl]-1-ethoxy]phenyl]-3-[4-[(morpholin-4yl)carbonyl]-1,3-oxazol-2-yl]butanoic acid;

(±)-4-[4-[2-[6-(methylamino)pyridin-2-yl]-1-ethoxy]phenyl]-3-[4-[[N-methyl-N-(2,2,2-trifluoroethyl)amino]carbonyl]-1,3-oxazol-2-yl]butanoic acid;

(±)-4-[4-[2-[6-(methylamino)pyridin-2-yl]-1-ethoxy]phenyl]-3-[4-(trifluoromethyl)thiazol-2-yl]butanoic acid;

(±)-4-[4-[2-[6-(methylamino)pyridin-2-yl]-1-ethoxy]phenyl]-3-(3-methylthiazol-2-yl)butanoic acid;

(S)-3-(3-fluorophenyl)-4[4-[2-(5,6,7,8-tetrahydro-1,8-naphthyridin-2-yl)ethoxy]phenyl]butanoic acid;

(±)-4-[4-[2-[6-(methylamino)pyridin-2-yl]ethoxy]phenyl]-3-(pyridin-3-yl)butanoic acid;

(S)-4-[4-[2-[6-(methylamino)pyridin-2-yl]ethoxy]phenyl]-3-(pyridin-3-yl)butanoic acid; and (S)-3-(pyridin-3-yl)4-[4-[2-(5,6,7,8-tetrahydro-1,8-naphthyridin-2-yl)ethoxy]phenyl]butanoic acid;

or a pharmaceutically acceptable salt thereof.

In cases wherein the compounds of this invention may have one or more chiral centers, unless specified, this invention includes each unique nonracemic compound which may be synthesized and resolved by conventional techniques.

In cases in which compounds have unsaturated carbon—carbon double bonds, both the cis (Z) and trans (E) isomers are within the scope of this invention. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in viv. Thus, in another aspect of this invention are novel prodrugs, which are also intermediates in the preparation of formula (Ia) compounds, of formula (II):

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem,* 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl. Any $C_{1-4}$alkyl may be optionally substituted with the group $R^X$, which may be on any carbon atom that results in a stable structure and is available by conventional synthetic techniques. Suitable-groups for RX are $C_{1-4}$alkyl, OR*, SR*, $C_{1-4}$alkylsulfonyl, $C_{1-4}$alkylsulfoxyl, —CN, N(R*)$_2$, $CH_2N(R^*)_2$, —NO$_2$, —CF$_3$, —CO$_2$R* —CON(R*)$_2$, —COR*, —SO$_2$N(R*)$_2$, —NR*C(O)R*, F, Cl, Br, I, or CF$_3$S(O)$_r$—, wherein r is 0, 1 or 2, and R* is H, $C_{1-4}$alkyl, phenyl or benzyl.

Halogen or halo means F, Cl, Br, and I.

Ar, or aryl, as applied herein, means phenyl or naphthyl, or phenyl or naphthyl substituted by one to three substituents, such as those defined above for alkyl, especially $C_{1-4}$alkyl, $C_{1-4}$alkoxy, $C_{1-4}$alkylthio, CF$_3$, NH$_2$, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuran, benzimidazole, benzopyran, benzothiophene, benzothiazole, furan, imidazole, indoline, morpholine, piperidine, piperazine, pyrrole, pyrrolidine, tetrahydropyridine, pyridine, thiazole, oxazole, thiophene, quinoline, isoquinoline, and tetra- and perhydro-quinoline and isoquinoline. Any accessible combination of up to three substituents on the Het ring, such as those defined above for alkyl, that are available by chemical synthesis and are stable are within the scope of this invention.

Certain radical groups are abbreviated herein, t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

Compounds of this invention are prepared by the general methods described in Schemes I-VI.

Scheme 1

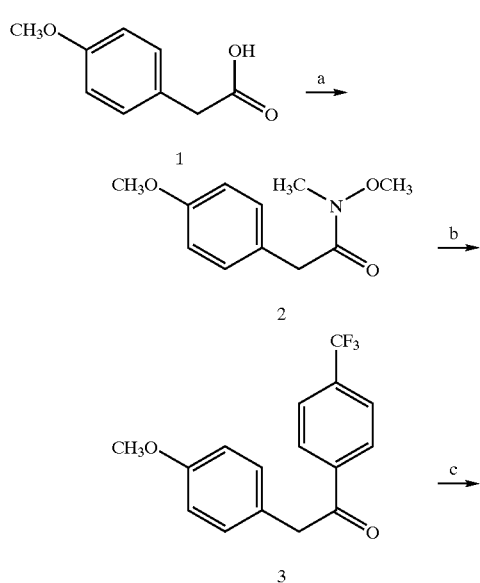

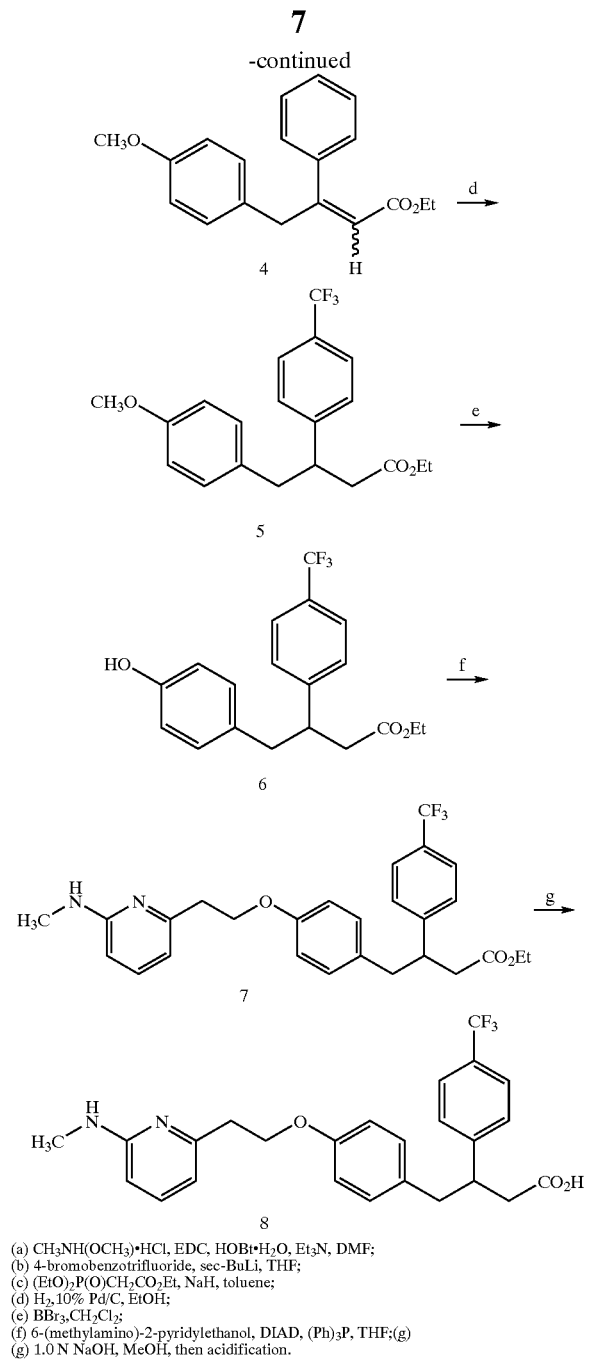

(a) CH₃NH(OCH₃)•HCl, EDC, HOBt•H₂O, Et₃N, DMF;
(b) 4-bromobenzotrifluoride, sec-BuLi, THF;
(c) (EtO)₂P(O)CH₂CO₂Et, NaH, toluene;
(d) H₂,10% Pd/C, EtOH;
(e) BBr₃,CH₂Cl₂;
(f) 6-(methylamino)-2-pyridylethanol, DIAD, (Ph)₃P, THF;(g)
(g) 1.0 N NaOH, MeOH, then acidification.

An appropriate alkoxyphenylacetic acid, for instance 4-methoxyphenylacetic acid (I-1), is converted to the deoxybenzoin derivative I-3 by reaction of the corresponding N-methoxy-N-methylamide (I-2) with a metalated aromatic derivative, according to the general method of Weinreb (*Tetrahedron Lett* 1981, 22, 3815). Compound I-3 is converted to the α,β-unsaturated ester I-4 through the well-known Wittig reaction. Optimally, the reaction is conducted using triethyl phosphonoacetate in the presence of a suitable base, generally sodium hydride or lithium bis(trimethylsilyl) amide, in an aprotic solvent, such as toluene, THF, or mixtures thereof. Reduction of the olefin group of 14 is optimally accomplished by hydrogenation in the presence of a palladium catalyst, for instance palladium on activated charcoal, in a suitable solvent, such as EtOAc, MeOH, EtOH, i-PrOH, or mixtures thereof. The methyl ether of I-5 can be cleaved with boron tribromide (BBr₃), in an inert solvent, preferably CH₂Cl₂, or with ethanethiol (EtSH) and aluminum trichloride (AlCl₃) in an inert solvent, such as CH₂Cl₂. Other useful methods for removal of methyl ether protecting groups are described in Greene, "Protective Groups in Organic Synthesis" (published by Wiley-Interscience). The resulting phenol 1.6 is reacted with 6-(methylamino)-2-pyridylethanol in a Mitsunobu-type coupling reaction (*Organic Reactions* 1992, 42, 335–656; *Synthesis* 1981, 1–28) to afford 1-7. The reaction is mediated by the complex formed between an azodicarboxylate diester, such as diethyl azodicarboxylate or diisopropyl azodicarboxylate, and triphenylphosphine, and is conducted in an aprotic solvent, for instance THF, CH₂Cl₂, or DMF. The ethyl ester of 1-7 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid 1-8. Alternatively, the intermediate carboxylate salt can be isolated, if desired, or a carboxylate salt of the free carboxylic acid can be prepared by methods well-known to those of skill in the art.

Scheme II

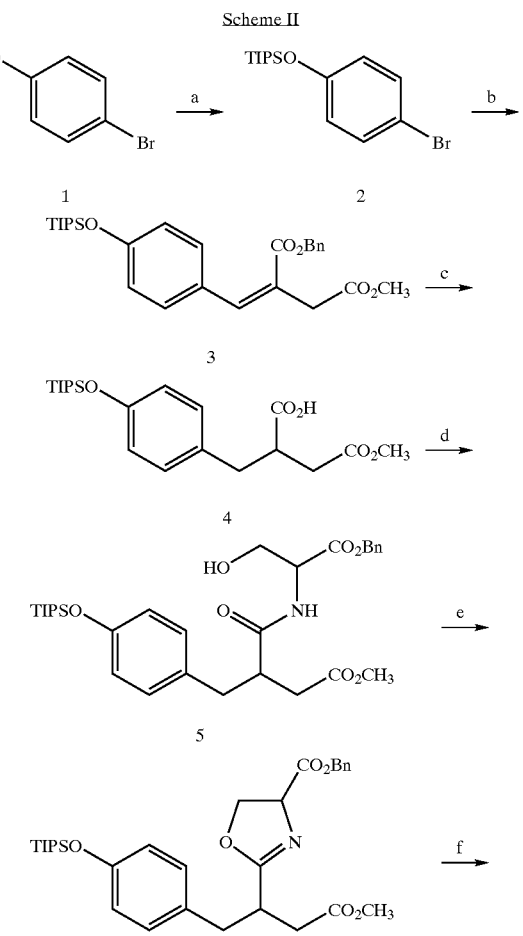

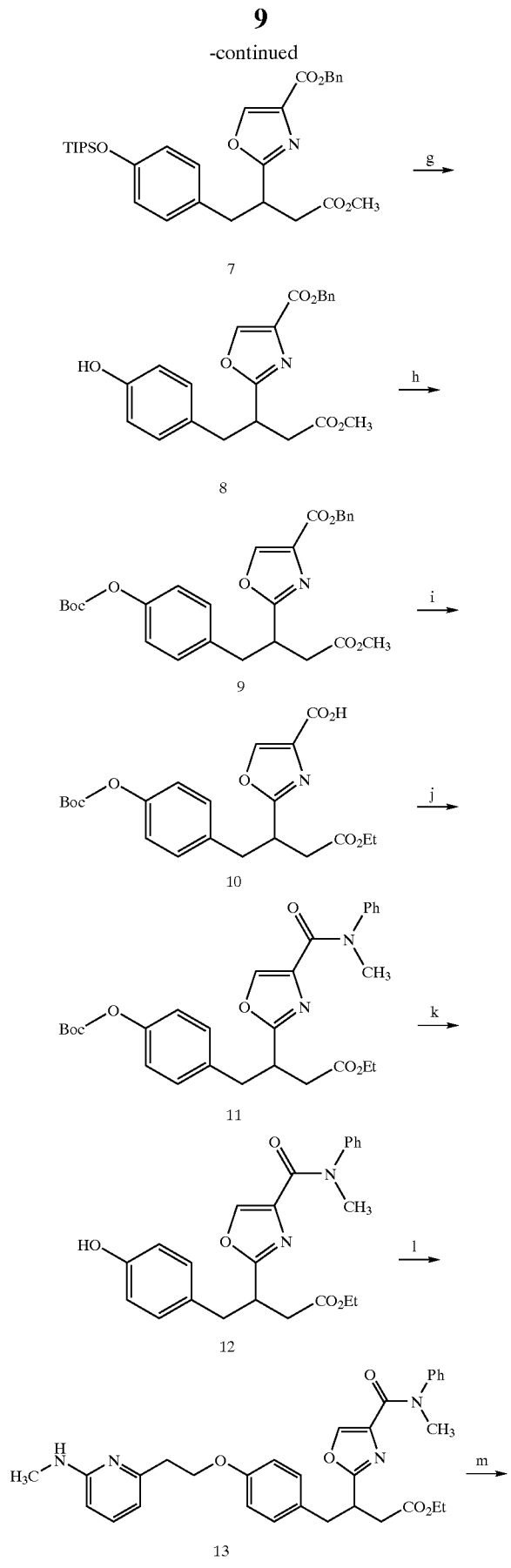

(a) Triisopropylsilyl chloride, imidazole, DMF;
(b) methyl 3-(benzyloxycarbonyl)-3-butenoate, Pd(OAc)$_2$,P(tol)$_3$,(i-Pr)$_2$NEt, propionitrile;
(c) H$_2$, 10% Pd/C, EtOAc;
(d) serine benzyl ester hydrochloride, EDC, HOBt•H$_2$O, Et$_3$N, DMF;
(e) Burgess reagent, THF;
(f) Cl$_3$CBr, DBU, CH$_2$Cl$_2$;
(g) TBAF, THF;
(h) (Boc)$_2$O, pyridine, THF;
(i) H$_2$, 10% Pd/C, EtOH;
(j) N-methylaniline, EDC, BPFFH, (i-Pr)$_2$NEt, pyridine, DMF;
(k) 4 N HCl/dioxane;
(l) 6-(methylamino)-2-pyridylethanol, DIAD, (Ph)$_3$P, THF;
(m) LiOH, THF, H$_2$O, then acidification.

A halophenol derivative, for instance 4-bromophenol (II-1), is converted to a suitably protected derivative, for instance 4-bromo-1-(triisopropylsilyloxy)benzene (II-2). The protecting group for the phenol must be compatible with subsequent chemistry, and also must be able to be removed selectively when desired. Methods for the protection of phenols are described in standard reference volumes, such as Greene, "Protective Groups in Organic Synthesis" (published by Wiley-Interscience). Compound II-2 reacts with methyl 3-(benzyloxycarbonyl)-3-butenoate in a Heck-type reaction (see Heck, Org. Reactions 1982, 27, 345) to afford II-3. The reaction is mediated by a palladium(0) species, and generally is conducted in an inert solvent, such as CH$_3$CN, propionitrile, or toluene, in the presence of an appropriate acid scavenger, such as triethylamine (Et$_3$N) or diisopropylethylamine ((i-Pr)$_2$NEt). Typical sources of the palladium(0) species include palladium (II) acetate (Pd(OAc)$_2$) and palladium(II) chloride (PdCl$_2$), and oftentimes phosphine ligands, for instance triphenylphosphine (PPh$_3$) or tri-ortho-tolylphosphine (P(tol)$_3$), are included. The α,β-unsaturated ester II-3 is reduced to the saturated compound II-4 by reaction with hydrogen gas in the presence of a suitable catalyst, preferably palladium metal on activated carbon (Pd/C), in an inert solvent, generally MeOH, EtOH, EtOAc, or mixtures thereof. The carboxylic acid of II-4 is converted to an activated form using, for example, EDC and HOBt, SOCl$_2$, or 1,1'-carbonyldiimidazole (CDI), and the activated form is subsequently reacted with an appropriate amine, for instance serine benzyl ester, in a suitable solvent, such as DMF, to afford II-5. Depending on whether acid neutralization is required, an added base, such as triethylamine (Et$_3$N), diisopropylethylamine ((i-Pr)$_2$NEt), or pyridine, may be used. Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag). II-5 is then converted to the oxazole derivative II-7. Several methods are known for the conversion of amidoalcohols to oxazoles (Meyers, *Tetrahedron* 1994, 50, 2297–2360; Wipf, *J. Org. Chem* 1993, 58, 3604–3606). For example, the amidoalcohol II-5 can be converted first to the oxazoline II-6. This transformation is generally accomplished under dehydrating conditions, such as reaction with Burgess reagent in THF. Oxazoline II-6 is then oxidized to oxazole II-7 using, for instance, bromtrichloromethane and DBU in CH$_2$Cl$_2$ (Williams, *Tetrahedron Letters* 1997, 38, 331–334) or CuBr$_2$ and DBU in an appropriate solvent, such as EtOAc/CHCl$_3$ or CH$_2$Cl$_2$ (Barrish, *J. Org. Chem.* 1993, 58, 4494–4496). Removal of the silyl protecting group under standard fluoride conditions (see Greene above) affords phenol II-8, which is converted to the tert-butyloxy carbonate derivative II-9 using di-tert-butyl dicarbonate in the presence of a base, generally pyridine, in a polar, neutral solvent, such as THF. This new protecting group is selected as described above. Compound II-9 is converted to the carboxylic acid derivative II-10 by hydrogenation as described above, and II-10 is converted to amide II—II according to the general procedure of Carpino and Ayman (*J. Am. Chem. Soc.* 1995, 117, 5401–5402). Under these conditions, carboxylic acid II-10 is reacted with a suitable amine, for instance N-methylaniline, in the presence of bis(tetramethylene)fluoroformamidinium hexafluorophosphate (BPFFH) and an appropriate base, generally Et$_3$N, (i-Pr)$_2$NEt, pyridine, or mixtures thereof, in a polar, neutral solvent, such as DMF. The tert-butyloxy carbamate protecting group is removed under standard acidic conditions (see Greene above), and the resulting phenol II-12 is converted to II-14 by the methods described in Scheme 1.

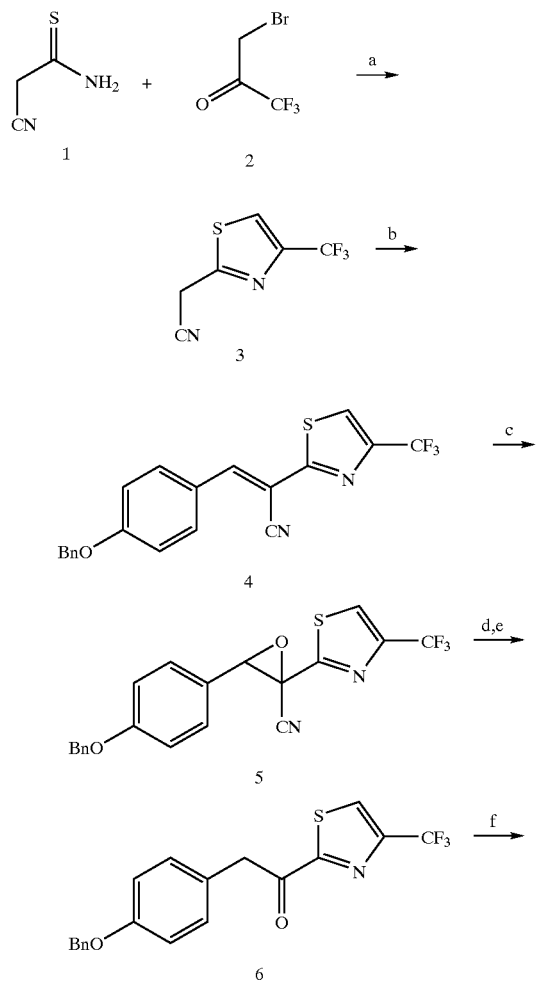

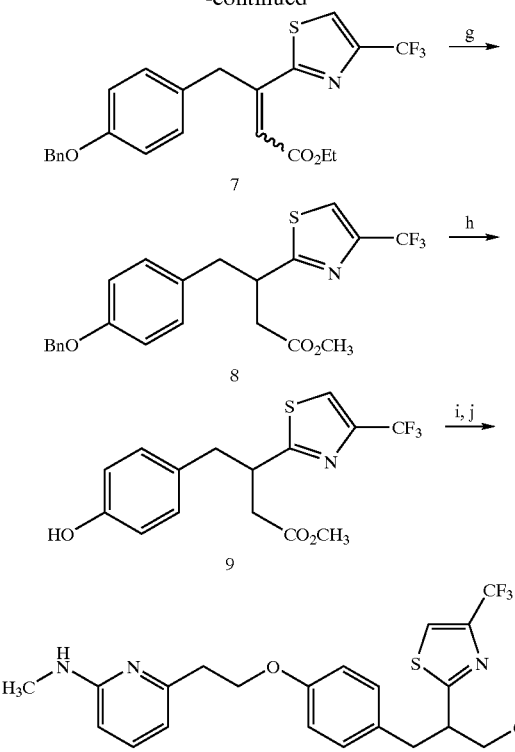

(a) EtOH, reflux;
(b) 4-(benzyloxy)benzaldehyde, NaOEt, EtOH;
(c) Al$_2$O$_3$, NaOCl, CH$_3$CN;
(d) Et$_3$SiH, BF$_3$•OEt$_2$,CH$_2$Cl$_2$;
(e) n-Bu$_4$NF, THF;
(f) (EtO)$_2$P(=O)CH$_2$CO$_2$Et, NaH, THF, reflux;
(g) Mg, MeOH;
(h) BF$_3$•OEt$_2$, EtSH;
(i) 6-(methylamino)-2-pyridylethanol, DIAD,(Ph)$_3$P, THF;
(j) LiOH, THF, H$_2$O, then acidification.

Thiazole derivative III-3 is prepared by condensation of 2-cyanoacetamide (III-1) and 3-bromo-1,1,1-trifluoroacetone (III-2) in refluxing ethanol, by appropriate modification of the procedure of Schaefer and Gewald (*J. Prakt. Chem.* 1974, 316, 684–692) for the preparation of 4-phenyl-2-(cyanomethyl)thiazole. Aldol condensation of III-3 with an appropriately substituted benzaldehyde derivative, for example 4 (benzyloxy)benzaldehyde, gives III-4. The reaction is catalyzed by a suitable base, preferably sodium ethoxide, and is conducted in a polar solvent, generally ethanol. Epoxidation of III-4 to afford III-5 is accomplished with sodium hypochlorite in the presence of neutral alumina according to the general method of Foucaud (Synthesis 1987, 9, 854–856). Other well-known epoxidation conditions, such as mCPBA, basic hydrogen peroxide, or basic tert-butyl hydroperoxide, might also be used, as long as the conditions are compatible with the functionality in the substrate. On exposure to triethylsilane in the presence of a suitable Lewis acid, such as BF$_3$.OEt$_2$, or a suitable protic acid, for instance TFA or HCl, the epoxide ring of III-5 is reductively opened in a highly regioselective manner to afford ketone III-6, together with the corresponding trimethylsilyl cyanohydrin of the III-6. This cyanohydrin is conveniently converted to ketone III-6 on exposure to tetrabutylammonium fluoride in an appropriate solvent, generally THF. This ketone reacts in a Wittig-type reaction with triethyl phosphonoacetate in the presence of a suitable base, for instance LiN(TMS)$_2$ or NaH, in a polar, aprotic solvent, preferably THF, to afford the α,β-unsaturated ester III-7 as a mixture of olefinic isomers. On reaction with magnesium metal in MeOH, the olefin of III-7 is selectively reduced to afford the saturated derivative III-8. The ethyl ester is converted to a methyl ester under these conditions. Removal of the benzyl group is accomplished with ethanethiol and BF$_3$.OEt$_2$, to afford the phenol III-9, which is converted to III-10 according to the methods described in Scheme I.

methylthiazole, prepared from 5-methylthiazole and n-butyllithium, reacts with IV-2 in an ethereal solvent, such as THF or DME, to afford the ketone derivative IV-3. This ketone is then converted to TV-6 according to the methods described in Scheme III.

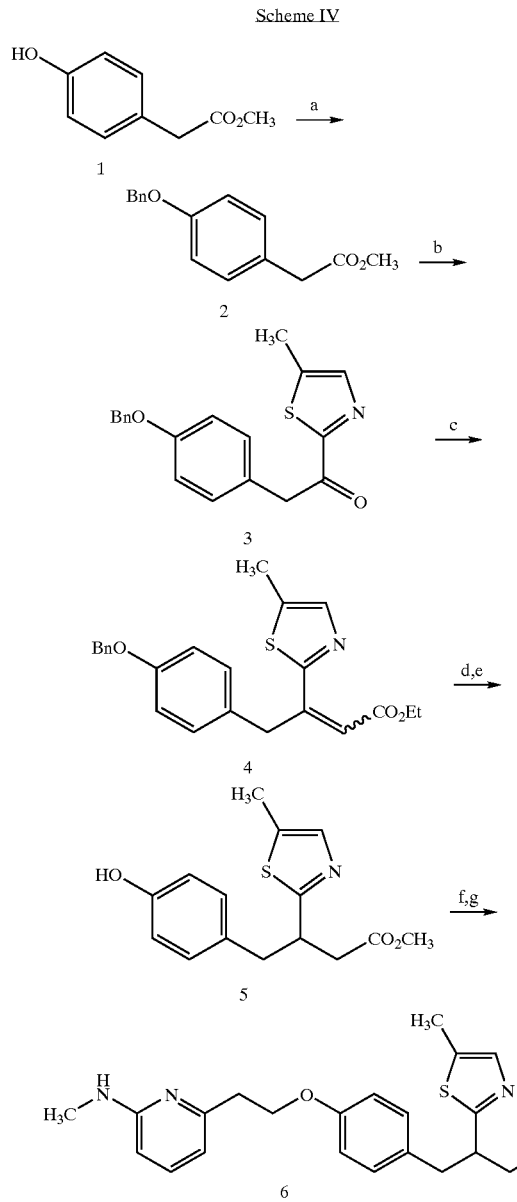

(a) BnCl, K$_2$CO$_3$, acetone;
(b) 5-methylthiazole, n-BuLi, THF;
(c) (EtO)$_2$P(=O)CH$_2$CO$_2$Et, NaH, THF;
(d) Mg, MeOH;
(e) BF$_3$·OEt$_2$, EtSH;
(f) 6-(methylamino)-2-pyridylethanol, DIAD, (Ph)$_3$P, THF;
(g) LiOH, THF, H$_2$O, then acidification.

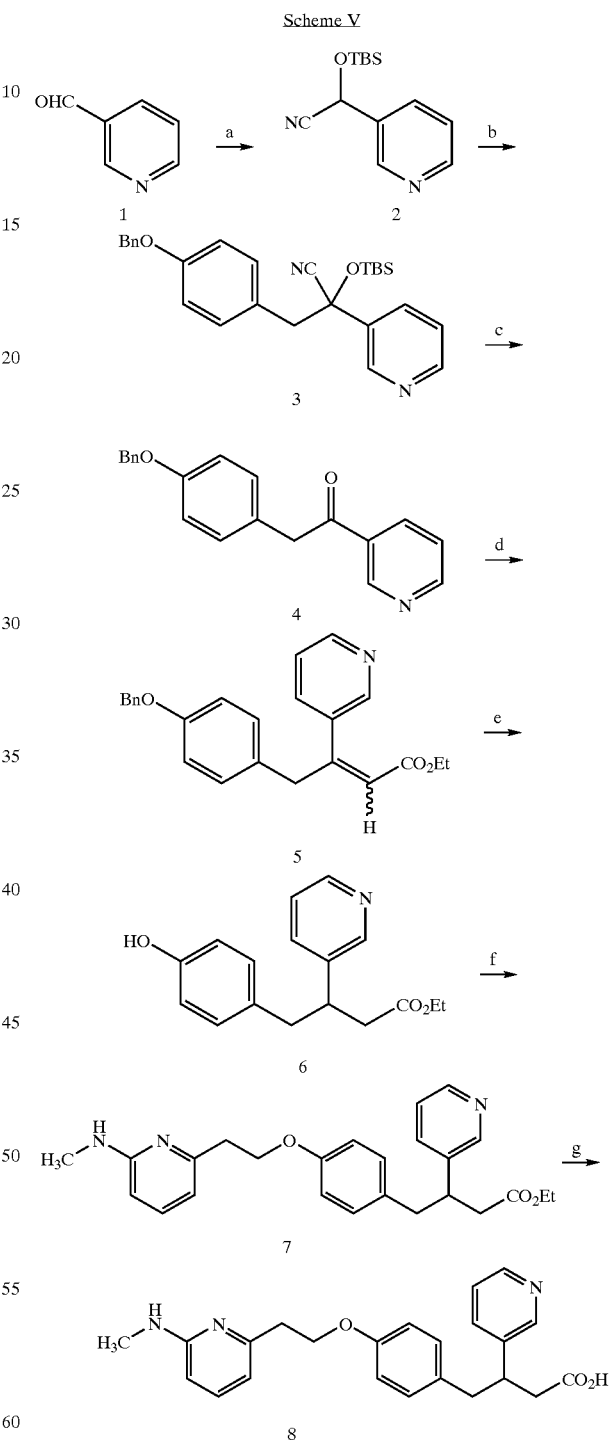

(a) TBDMSCl, KCN, ZnI$_2$, CH$_3$CN;
(b) LDA, THF, then 4-benzyloxybenzyl chloride;
(c) TBAF, THF;
(d) (EtO)$_2$P(=O)CH$_2$CO$_2$Et, NaH, THF;
(e) H$_2$Pd/C,EtOH;
(f) 6-(methylamino)-2-pyridylethanol, DIAD, (Ph)$_3$P,THF;
(g) LiOH, THF, H$_2$O, then acidification.

The phenol group of commercially available methyl 4-hydroxyphenylacetate (V-1) is protected with a suitable protecting group, for instance a methyl ether, a benzyl ether, or a triisopropylsilyl ether. Protection of phenols is well-known to those of skill in the art, and representative protecting groups are described in standard reference volumes such as Greene "Protective Groups in Organic Synthesis" (published by Wiley-Interscience). The resulting compound (IV-2) reacts with suitable Grignard or organolithium reagents to afford ketones. For example, 2-lithio-5-

A selected aromatic aldehyde, for example 3-pyridinecarboxaldehyde (V-1), is converted to a silyl-protected cyanohydrin such as V-2 by reaction with cyanide ion in the presence of a suitable silyl halide, for instance trimethylsilyl chloride (TMSCl), triisopropylsilyl chloride (TIPSCl), or tert-butyldimethylsilyl chloride (TBDMSCl or TBSCl). Typical sources of cyanide ion include potassium cyanide (KCN), sodium cyanide (NaCN), and tetrabutylammonium cyanide (Bu₄NCN). The reaction is frequently conducted in the presence of a catalytic amount of a Lewis acid, generally ZnI₂, and a polar, aprotic solvent, such as acetonitrile (CH₃CN), is preferred. Other protected cyanohydrins, for instance an ethoxyethyl-protected cyanohydrin, may be used, as long as the protecting group is compatible with subsequent chemistry and can be selectively removed when desired. A discussion of protecting groups can be found in standard reference volumes, such as Greene, "Protective Groups in Organic Synthesis" (published by Wiley-Interscience). Compound V-2 is C-alkylated with an appropriate benzyl halide, for example 4-benzyloxybenzyl chloride, to afford V-3. The reaction involves an initial deprotonation to afford an intermediate anion, which is not isolated but rather is reacted in situ with the alkylating agent. Typical bases for this type of reaction include lithium diisopropylamide (LDA) and lithium hexamethyldisilazide (LiN(TMS)₂), and polar, aprotic solvents such as THF or DME are preferred. The TBS-cyanohydrin of V-3 is conveniently converted to the ketone V-4 by reaction with tetrabutylammonium fluoride (TBAF). A two step procedure might also be used to effect this transformation. For example, the silyl protecting group of V-3 can be removed under acidic conditions, such as by reaction with HF, to afford a cyanohydrin which can be converted to ketone V-4 by reaction with a suitable base. Compound V-4 is converted to the α,β-unsaturated ester V-5 through the well-known Wittig reaction. Typically, the reaction is conducted using triethyl phosphonoacetate in the presence of a suitable base, generally sodium hydride (NaH) or LiN(TMS)₂, in an aprotic solvent, such as toluene, THF, or mixtures thereof. Reduction of the olefin group of V-5 is optimally accomplished by hydrogenation in the presence of a palladium catalyst, for instance palladium on activated charcoal, in a suitable solvent, such as EtOAc, MeOH, EtOH, i-PrOH, or mixtures thereof. Under these conditions, the benzyl protecting group on the phenol is also removed. The resulting phenol V-6 is reacted with 6(methylamino)-2-pyridylethanol in a Mitsunobu-type coupling reaction (*Organic Reactions* 1992, 42, 335-656; *Synthesis* 1981, 1-28) to afford V-7. The reaction is mediated by the complex formed between an azodicarboxylate diester, such as diethyl azodicarboxylate or diisopropyl azodicarboxylate, and triphenylphosphine, and is typically conducted in an aprotic solvent, for instance THF, CH₂Cl₂, or DMF. The ethyl ester of V-7 is hydrolyzed using aqueous base, for example, LiOH or NaOH in aqueous dioxane, THF, methanol or ethanol, and the intermediate carboxylate salt is acidified with a suitable acid, for instance TFA or HCl, to afford the carboxylic acid V-8. If desired, the intermediate carboxylate salt can be isolated. In addition, appropriate salts of the carboxylic acid or the amine can be prepared by methods well-known to those of skill in the art.

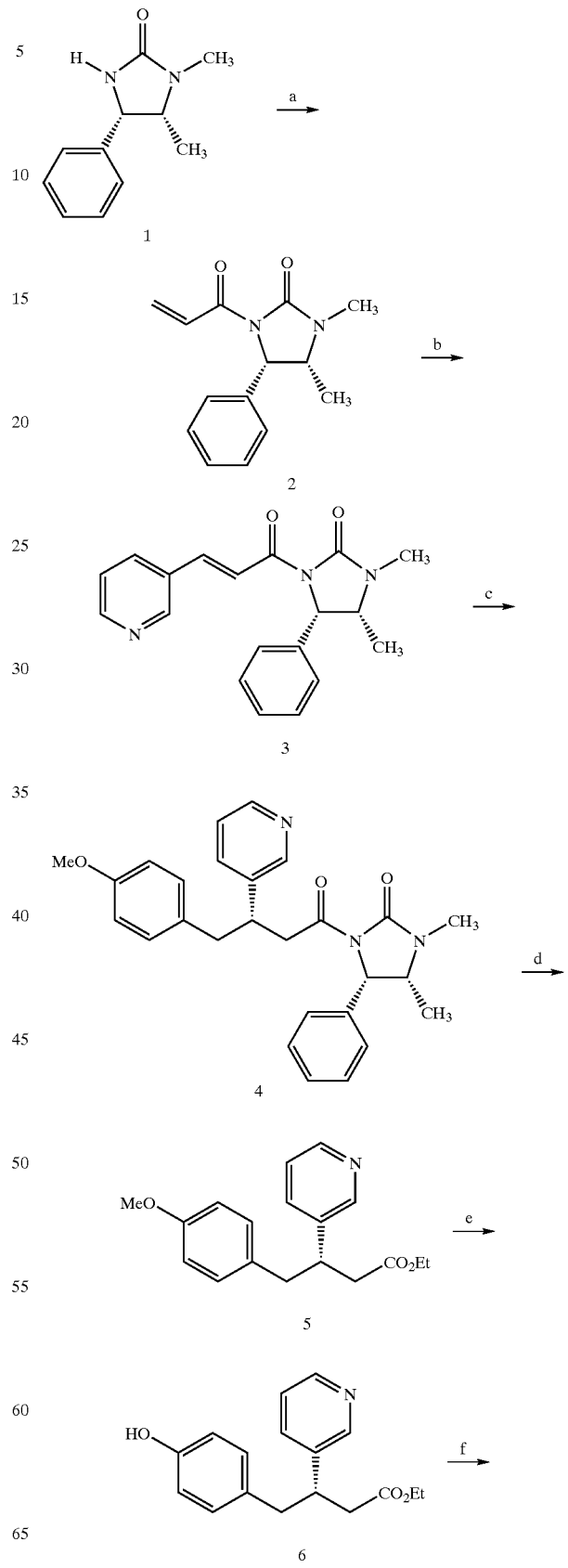

Scheme VI

-continued

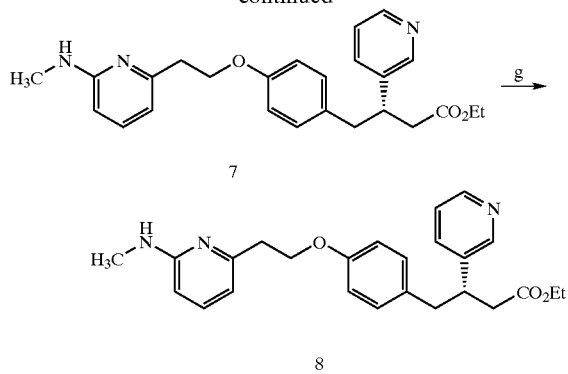

(a) acryloyl chloride, (i-Pr)₂NEt, CuCl, CH₂Cl₂;
(b) 3-bromopyridine, Pd(OAc)₂, P(tol)₃, (i-Pr)₂NEt, DMF;
(c) 4-methoxybenzylmagnesium chloride, ZnI₂,
 CuBr•DMS, THF, toluene;
(d) NaOEt, THF;
(e) AlCl₃, EtSH, CH₂Cl₂;
(f) 6-(methylamino)-2-pyridylethanol, DIAD, (Ph)₃P, THF;
(g) NaOH, dioxane, H₂O, then acidification.

Commercially available (4S, 5R)-1,5-dimethyl-4-phenyl-2-imidazolidinone (VI-1) reacts with an appropriate α,β-unsaturated acid chloride, for instance acryloyl chloride, to afford imide VI-2. The reaction is mediated by a suitable base, typically triethylamine (Et₃N) or diisopropylethylamine ((i-Pr)₂NEt), and is conducted in the presence of a catalytic amount of a cuprous halide, for instance copper (I) chloride. A neutral solvent such as CH₂Cl₂ is preferred. Compound VI-2 reacts with a suitable aryl halide, such as 3-bromopyridine, in a Heck-type reaction (see Heck, Org. Reactions 1982, 27, 345) to afford VI-3. The reaction is mediated by a palladium(0) species, and generally is conducted in an inert solvent, such as CH₃CN, propionitrile, toluene, or DMF, in the presence of an appropriate acid scavenger, such as triethylamine (Et₃N) or diisopropylethylamine ((i-Pr)₂NEt). Typical sources of the palladium(0) species include palladium (II) acetate (Pd(OAc)₂) and palladium(II) chloride (PdCl₂), and oftentimes phosphine ligands, for instance triphenylphosphine (PPh₃) or tri-ortho-tolylphosphine (P(tol)₃), are included. Compound VI-3 reacts with an organocopper species in a 1,4-addition reaction to give the conjugate addition product VI4 (see Melnyk, O.; Stephan, E.; Pourcelot, G.; Cresson, P. *Tetrahedron* 1992, 48, 841–850; Bongini, A.; Cardillo, G.; Mingardi, A.; Tomasini, C. *Tetrahedron Asymmetry* 1996, 7, 1457–1466; van Heerden, P. S.; Bezuidenhoudt, B. C. B.; Ferreira, D. *Tetrahedron Lett.* 1997, 38, 1821–1824. For reviews on organocopper reactions, see Posner, G. *Organic Reactions* 1972, 19, 1–113; Lipshutz, B. *Organic Reactions* 1992, 41, 135–631). Generation of the organocopper species can be accomplished by the addition of an organolithium or organomagnesium reagent, for instance 4-methoxybenzylmagnesium chloride, to a copper (1) source, for example CuCl, CuBr.DMS, or CuI, in an inert solvent, such as Et₂O, THF, DME, toluene, or mixtures thereof. The diastereoselectivity of the reaction can be enhanced by certain Lewis acids, for instance, MgBr₂, Bu₂BOTf, or ZnI₂. The chiral auxiliary of VI-14 is conveniently removed by ethanolysis under basic conditions. For example, treatment of VI-4 with sodium ethoxide in THF affords VI-5. The methyl ether of VI-5 can be cleaved with boron tribromide (BBr₃), in an inert solvent, preferably CH₂Cl₂, or with ethanethiol (EtSH) and aluminum trichloride (AlCl₃) in an inert solvent, such as CH₂Cl₂, to afford phenol VI6. Other useful methods for removal of methyl ether protecting groups are described in standard reference volumes (see Scheme V). Phenol VI-6 is converted to VI-8 as described in Scheme V.

Amide coupling reagents as used herein denote reagents which may be used to form peptide bonds. Typical coupling methods employ carbodiimides, activated ahydrides and esters and acyl halides. Reagents such as EDC, DCC, DPPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem,* 29, 984 (1986) and *J. Med. Chem.,* 30, 2291 (1987) are generally illustrative of the technique and are incorporated herein by reference.

Typically, the amine or aniline is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

Useful intermediates for preparing formula (I) compounds in which R² is a benzimidazole are disclosed in Nestor et al, *J. Med. Chew* 1984, 27, 320. Representative methods for preparing benzimidazole compounds useful as intermediates in the present invention are also common to the art and may be found, for instance, in EP-A 0 381 033.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li⁺, Na⁺, K⁺, Ca⁺⁺, Mg⁺⁺ and NH₄⁺ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, anti-angiogenic, anti-inflammatory and anti-metastatic agents, and be useful in the treatment of atherosclerosis and restenosis.

The compound is administered either orally or parenterally to the patient, in a manner such that the concentration of drug is sufficient to inhibit bone resorption, or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

This invention further provides a method for treating osteoporosis or inhibiting bone loss which comprises administering stepwise or in physical combination a compound of formula (1) and other inhibitors of bone resorption, such as bisphosphonates (i.e., allendronate), hormone replacement therapy, anti-estrogens, or calcitonin. In addition, this invention provides a method of treatment using a compound of this invention and an anabolic agent, such as the bone morphogenic protein, iproflavone, useful in the prevention of bone loss and/or to increase bone mass.

Additionally, this invention provides a method of inhibiting tumor growth which comprises administering stepwise or in physical combination a compound of formula (I) and an antineoplastic agent. Compounds of the camptothecin analog class, such as topotecan, irinotecan and 9-aminocamptothecin, and platinum coordination complexes, such as cisplatin, ormaplatin and tetraplatin, are well known groups of antineoplastic agents. Compounds of the camptothecin analog class are described in U.S. Pat. Nos. 5,004,758, 4.604,463, 4,473,692, 4,545,880 4,342,776, 4,513,138, 4,399,276, EP Patent Application Publication Nos. 0 418 099 and 0 088 642, Wani, et al., *J. Med. Chem.*, 1986, 29, 2358, Wani, et al., *J. Med. Chem.*, 1980, 23, 554, Wani, et al., *J. Med. Chem.*, 1987, 30, 1774, and Nitta, et al., Proc. 14*th International Congr. Chemotherapy.*, 1985, *Anticancer Section* 1, 28, the entire disclosure of each which is hereby incorporated by reference. The platinum coordination complex, cisplatin, is available under the name Platinol® from Bristol Myers-Squibb Corporation. Useful formulations for cisplatin are described in U.S. Pat. Nos. 5,562,925 and 4,310,515, the entire disclosure of each which is hereby incorporated by reference.

In the method of inhibiting tumor growth which comprises administering stepwise or in physical combination a compound of formula (I) and an antineoplastic agent, the platinum coordination compound, for example cisplatin, can be administered using slow intravenous infusion. The preferred carrier is a dextrose/saline solution containing mannitol. The dose schedule of the platinum coordination compound may be on the basis of from about 1 to about 500 mg per square meter ($mg/m^2$) of body surface area per course of treatment. Infusions of the platinum coordiation compound may be given one to two times weekly, and the weekly treatments may be repeated several times. Using a compound of the camptothecin analog class in a parenteral administration, the course of therapy generally employed is from about 0.1 to about 300.0 $mg/m^2$ of body surface area per day for about five consecutive days. Most preferably, the course of therapy employed for topotecan is from about 1.0 to about 2.0 $mg/m^2$ of body surface area per day for about five consecutive days. Preferably, the course of therapy is repeated at least once at about a seven day to about a twenty-eight day interval.

The pharmaceutical composition may be formulated with both the compound of formula (I) and the antineoplastic agent in the same container, but formulation in different containers is preferred. When both agents are provided in solution form, they can be contained in an infusion/injection system for simultaneous administration or in a tandem arrangement.

For convenient administration of the compound of formula (I) and the antineoplastic agent at the same or different times, a kit is prepared, comprising, in a single container, such as a box, carton or other container, individual bottles, bags, vials or other containers each having an effective amount of the compound of formula (I) for parenteral administration, as described above, and an effective amount of the antineoplastic agent for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the antineoplastic agent and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the compound of formula (I) may be in an i.v. injectable form, or infusion bag linked in series, via tubing, to the antineoplastic agent in a second infusion bag. Using such a system, a patient can receive an initial bolus-type injection or infusion of the compound of formula (I) followed by an infusion of the antineoplastic agent.

The compounds may be tested in one of several biological assays to determine the concentration of compound which is required to have a given pharmacological effect.

Inhibition of vitronectin binding

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, N.Y., N.Y.) at 0.1 mL per well. 0.1–0.2 µg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4). 100 mM NaCl, 1 mM $CaCl_2$, 1 mM $MnCl_2$, 1 mM $MgCl_2$) to a final compound concentration of 100 µM. This solution is then diluted to the required final compound concentration. Various concentrations of unlabeled antagonists (0.001–100 µM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 µM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The Ki (dissociation constant of the antagonist) was calculated according to the equation: $Ki=IC_{50}/(1+L/K_d)$, where L and $K_d$ were the concentration and the dissociation constant of [3H]-SK&F-107260, respectively.

Compounds of the present invention inhibit vitronectin binding to SK&F 107260 in the concentration range of about 0.060 to about 0.0005 micomolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

Vascular Smooth Muscle Cell Migration Assay

Rat or human aortic smooth muscle cells were used. The cell migration was monitored in a Transwell cell culture chamber by using a polycarbonate membrane with pores of 8 µm (Costar). The lower surface of the filter was coated with vitronectin. Cells were suspended in DMEM supplemented with 0.2% bovine serum albumin at a concentration of 2.5–5.0×10⁶ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% $CO_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Thyroparathyroidectomized Rat Model

Each experimental group consists of 5-6 adult male Sprague-Dawley rats (250–400 g body weight). The rats are thyroparathyroidectomized (by the vendor, Taconic Farms) 7 days prior to use. All rats receive a replacement dose of thyroxine every 3 days. On receipt of the rats, circulating ionized calcium levels are measured in whole blood immediately after it has been withdrawn by tail venipuncture into heparinized tubes. Rats are included if the ionized Ca level (measured with a Ciba-Corning model 634 calcium pH analyzer) is <1.2 mM/L. Each rat is fitted with an indwelling venous and arterial catheter for the delivery of test material and for blood sampling respectively. The rats are then put on a diet of calcium-free chow and deionized water. Baseline Ca levels are measured and each rat is administered either control vehicle or human parathyroid hormone 1-34 peptide (hPTH1-34, dose 1.25 µg/kg/h in saline/0.1% bovine serum albumin, Bachem, Ca) or a mixture of hPTH1-34 and test material, by continuous intravenous infusion via the venous catheter using an external syringe pump. The calcemic response of each rat is measured at two-hourly intervals during the infusion period of 6–8 hours.

HUMAN Osteoclast Resorption and Adhesion Assays

Pit resorption and adhesion assays have been developed and standardized using normal human osteoclasts derived from osteoclastoma tissue. Assay 1 was developed for the measurement of osteoclast pit volumes by laser confocal microscopy. Assay 2 was developed as a higher throughput screen in which collagen fragments (released during resorption) are measured by competitive ELISA.

Assay 1 (Using Laser Confocal Microscopy)

Aliquots of human osteoclastoma-derived cell suspensions are removed from liquid nitrogen strorage, warmed rapidly at 37° C. and washed x1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed x2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

3 ml aliquots of the cell suspension (per compound treatment) are decanted into 15 ml centrifuge tubes. The cells are pelleted by centrifugation.

To each tube, 3 ml of the appropriate compound treatment are added (diluted to 50 uM in the EMEM medium). Also included are appropriate vehicle controls, a positive control (anti-vitronectin receptor murine monoclonal antibody [87MEM1] diluted to 100 ug/ml) and an isotype control ($IgG_{2a}$ diluted to 100 ug/ml). The samples are incubated at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml/well in a 6-well plate) and then placed into fresh medium containing the compound treatment or control samples. The samples are incubated at 37° C. for 48 hours.

Tartrate Resistant Acid Phosphatase (Trap) Procedure (Selective Stain for Cells of the Osteoclast Lineage)

The bone slices containing the attached osteoclasts are washed in phosphate buffered saline and fixed in 2% gluteraldehyde (in 0.2M sodium cacodylate) for 5 mins.

They are then washed in water and are incubated for 4 minutes in TRAP buffer at 37° C. (0.5 mg/ml naphthol AS-BI phosphate dissolved in N,N-dimethylformamide and mixed with 0.25 M citrate buffer (pH 4.5), containing 10 mM sodium tartrate.

Following a wash in cold water the slices are immersed in cold acetate buffer (0.1 M, pH 6.2) containing 1 mg/ml fast red garnet and incubated at 4° C. for 4 minutes.

Excess buffer is aspirated, and the slices are air dried following a wash in water.

The TRAP positive osteoclasts (brick red/purple precipitate) are enumerated by bright-field microscopy and are then removed from the surface of the dentine by sonication.

Pit volumes are determined using the Nikon/Lasertec ILM21W confocal microscope.

Assay 2 (Using an ELISA Readout)

The human osteoclasts are enriched and prepared for compound screening as described in the initial 9 steps of Assay 1. For clarity, these steps are repeated hereinbelow.

Aliquots of human osteoclastoma-derived cell suspensions are removed from liquid nitrogen strorage, warmed rapidly at 37° C. and washed x1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed x2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

In contrast to the method desribed above in Assay 1, the compounds are screened at 4 doses to obtain an $IC_{50}$, as outlined below:

The osteoclast preparations are preincubated for 30 minutes at 37° C. with test compound (4 doses) or controls.

They are then seeded onto bovine cortical bone slices in wells of a 48-well tissue culture plate and are incubated for a further 2 hours at 37° C.

The bone slices are washed in six changes of warm phosphate buffered saline (PBS), to remove non-adherent cells, and are then returned to wells of a 48 well plate containing fresh compound or controls.

The tissue culture plate is then incubated for 48 hours at 37° C.

The supernatants from each well are aspirated into individual tubes and are screened in a competitive ELISA that detects the c-telopeptide of type I collagen which is released during the resorption process. This is a commercially available ELISA (Osteometer, Denmark) that contains a rabbit antibody that specifically reacts with an 8-amino acid sequence (Glu-Lys-Ala-His-Asp- Gly-Gly-Arg) that is present in the carboxy-terminal telopeptide of the al-chain of type I collagen. The results are expressed as % inhibition of resorption compared to a vehicle control.

Human Osteoclast Adhesion Assay

The human osteoclasts are enriched and prepared for compound screening as described above in the inital 9 steps of Assay 1. For clarity, these steps are repeated hereinbelow.

Aliquots of human osteoclastoma-derived cell suspensions are removed from liquid nitrogen strorage, warmed rapidly at 37° C. and washed x1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed x2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated x10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

Osteoclastoma-derived osteoclasts are preincubated with compound (4 doses) or controls at 37° C. for 30 minutes.

The cells are then seeded onto osteopontin-coated slides (human or rat osteopontin, 2.5 ug/ml) and incubated for 2 hours at 37° C.

Non adherent cells are removed by washing the slides vigorously in phosphate buffered saline and the cells remaining on the slides are fixed in acetone.

The osteoclasts are stained for tartrate-resistant acid phosphatase (TRAP), a selective marker for cells of this phenotype (see steps 15–17), and are enumerated by light microscopy. The results are expressed as % inhibition of adhesion compared to a vehicle control.

Cell Adhesion Assay

Cells and Cell Culture

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum, 1% glutamine and 1% Penicillin-Steptomycin.

Constructs and Transfections

A 3.2 kb EcoRI-KpnI fragment of the $\alpha_v$ subunit and a 2.4 kb XbaI-XhoI fragment of the $\beta_3$ subunit were inserted into the EcoRI-EcoRV cloning sites of the pCDN vector (Aiyar et al., 1994) which contains a CMV promoter and a G418 selectable marker by blunt end ligation. For stable expression, $80 \times 10^6$ HEK 293 cells were electrotransformed with $\alpha_v + \beta_3$ constructs (20 μg DNA of each subunit) using a Gene Pulser (Hensley et al., 1994) and plated in 100 mm plates ($5 \times 10^5$ cells/plate). After 48 hr, the growth medium was supplemented with 450 μg/mL Geneticin (G418 Sulfate, GIBCO-BRL, Bethesda, Md.). The cells were maintained in selection medium until the colonies were large enough to be assayed.

Immunocytochemical Analysis of Transfected Cells

To determine whether the HEK 293 transfectants expressed the vitronectin receptor, the cells were immobilized on glass microscope slides by centrifugation, fixed in acetone for 2 min at room temperature and air dried. Specific reactivity with 23C6, a monoclonal antibody specific for the $\alpha_v\beta_3$ complex was demonstrated using a standard indirect immunofluorescence method.

Cell Adhesion Studies

Corning 96-well ELISA plates were precoated overnight at 4° C. with 0.1 mL of human vitronectin (0.2 μg/mL in RPMI medium). At the time of the experiment, the plates were washed once with RPMI medium and blocked with 3.5% BSA in RPMI medium for 1 hr at room temperature. Transfected 293 cells were resuspended in RPMI medium, supplemented with 20 mM Hepes, pH 7.4 and 0.1% BSA at a density of $0.5 \times 10^6$ cells/mL. 0.1 mL of cell suspension was added to each well and incubated for 1 hr at 37° C., in the presence or absence of various $\alpha_v\beta_3$ antagonists. Following incubation, 0.025 mL of a 10% formaldehyde solution, pH 7.4, was added and the cells were fixed at room temperature for 10 min. The plates were washed 3 times with 0.2 mL of RPMI medium and the adherent cells were stained with 0.1 mL of 0.5% toluidine blue for 20 min at room temperature. Excess stain was removed by extensive washing with deionized water. The toluidine blue incorporated into cells was eluted by the addition of 0.1 mL of 50% ethanol containing 50 mM HCl. Cell adhesion was quantitated at an optical density of 600 nm on a microtiter plate reader (Titertek Multiskan MC, Sterling, Va.).

Solid-Phase $\alpha_v\beta_5$ Binding Assay:

The vitronectin receptor $\alpha_v\beta5$ was purified from human placenta. Receptor preparation was diluted with 50 mM Tris-HCl, pH 7.5, 100 mM NaCl, 1 mM $CaCl_2$, 1 mM $MnCl_2$, 1 mM $MgCl_2$ (buffer A) and was immediately added to 96-well ELISA plates at 0.1 ml per well. 0.1–0.2 μg of $\alpha_v\beta_3$ was added per well. The plates were incubated overnight at 4° C. At the time of the experiment, the wells were washed once with buffer A and were incubated with 0.1 ml of 3.5% bovine serum albumin in the same buffer for 1 hr at room temperature. Following incubation the wells were aspirated completely and washed twice with 0.2 ml buffer A.

In a [$^3$H]-SK&F-107260 competition assay, various concentrations of unlabeled antagonists (0.001–100 μM) were added to the wells, followed by the addition of 5.0 nM of [$^3$H]-SK&F-107260. The plates were incubated for 1 hr at room temperature. Following incubation the wells were aspirated completely and washed once with 0.2 ml of ice cold buffer A in a well-to-well fashion. The receptors were solubilized with 0.1 ml of 1% SDS and the bound [$^3$H]-SK&F-107260 was determined by liquid scintillation counting with the addition of 3 ml Ready Safe in a Beckman LS 6800 Liquid Scintillation Counter, with 40% efficiency. Nonspecific binding of [$^3$H]-SK&F-107260 was determined in the presence of 2 μM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to Cheng and Prusoff equation: $K_i=IC_{50}/(1+L/K_d)$, where L and $K_d$ were the concentration and the dissociation constant of [$^3$H]-SK&F-107260, respectively.

Inhibition of RGD-Mediated GPIIb-IIIa Binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70 C until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 μm hydrophilic durapore membranes. The wells were precoated with 0.2 mL of 10 μg/mL polylysine (Sigma Chemical Co., St. Louis. MO.) at room temperature for 1 h to block nonspecific binding. Various concentrations of unlabeled benzazepines were added to the wells in quadruplicate. [$^3$H]-SK&F-107260 was applied to each well at a final concentration of 4.5 nM, followed by the addition of 1 μg of the purified platelet GPIIb-IIIa-containing liposomes. The mixtures were incubated for 1 h at room temperature. The GPIIb IIIa-bound [3H]SK&F-107260 was separated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation. Ki —IC50/(I+L/Kd), where L is the concentration of [3H]-SK&F-07260 used in the competitive binding assay (4.5 nM), and $K_d$ is the dissociation constant of [3H]-SK&F-107260 which is 4.5 nM as determined by Scatchard analysis.

Preferred compounds of this invention have an affinity for the vitronectin receptor relative to the fibrinogen receptor of greater than 10:1. Most preferred compounds have a ratio of activity of greater than 100:1.

The efficacy of the compounds of formula (I) alone or in combination with an antineoplastic agent may be determined using several transplantable mouse tumor models. See U.S. Pat. Nos. 5,004,758 and 5,633,016 for details of these models.

The examples which follow are intended in no way to limit the scope of this invention, but are provided to illustrate how to make and use the compounds of this invention. Many other embodiments will be readily apparent to those skilled in the art.

General

Proton nuclear magnetic resonance ($^1$H NMR) spectra were recorded at either 250, 300, or 400 MHz. Chemical shifts are reported in parts per million (5) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. $CDCl_3$ is deuteriochloroform, DMSO-$d_6$ is hexadeuteriodimethylsulfoxide, and $CD_3OD$ is tetradeuteriomethanol. Infrared (IR) spectra were recorded in transmission mode, and band positions are reported in inverse wavenumbers ($cm^{-1}$). Mass spectra were obtained using electrospray (ES) or FAB ionization techniques. Elemental analyses were performed either in-house or by Quantitative Technologies Inc., Whitehouse, N. J. Melting points were taken on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5μ Apex-ODS indicates an octadecylsilyl derivatized silica gel chromatographic support having a nominal particle size of 5 u, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 6-(methylamino)-2-pyridylethanol a) 2-(ten-Butoxycarbonylamino)-6-picoline A solution of 2-amino-6-picoline (21.63 g, 200 mmole) and di-tert-butyl dicarbonate (52.38 g, 240 mmole) in CH₂Cl₂ (200 mL) was concentrated on the rotavap at 50° C. and the resulting residue was allowed to rotate on the rotavap at 50° C. under vacuum. After 21.5 hr, the reaction was diluted with hexanes (400 mL) and filtered through silica gel (hexanes followed by 20% EtOAc/hexanes). Concentration left the title compound (41.84 g, quantitative) as a light yellow oil which gradually solidified on standing: $^1$H NMR (250 MHz, CDCl₃) δ7.71 (d, J=8.3 Hz, 1 H), 7.40–7.65 (m, 2H), 6.80 (d, J=7.5 Hz, 1H), 2.43 (s, 3H), 1.50 (s, 9H); MS (ES) m/e 153 (M+H–C₄H₈)⁺.

b) 2-[(tert-Butoxycarbonyl)methylamino]-6-picoline

NaH (60% in mineral oil, 3.60 g, 90 mmole) was added in portions over several min to a solution of 2-(tert-butoxycarbonylamino-6-picoline (15.62 g, 75 mmole) and iodomethane (9.3 mL, 150 mmole) in anhydrous DMSO (75 mL) at 15° C. (cool water bath). The internal temperature rose to 35° C. When gas evolution had subsided, the cool water bath was removed and the reaction was allowed to stir at RT. After 0.5 hr, the dark yellow mixture was poured onto ice/H₂O (300 mL) and extracted with Et₂O (3×300 mL). The combined organic layers were washed sequentially with H₂O (2×75 mL) and brine (75 mL). Drying (MgSO₄) and concentration left a yellow oil which was chromatographed on silica gel (7% EtOAc/hexanes). The title compound (13.01 g, 78%) was obtained as a faintly yellow oil: $^1$H NMR (250 MHz, CDCl₃) δ 7.51 (app t, 1 H), 7.37 (d, J=8.2 Hz, 1 H), 6.86 (d, =7.2 Hz, 1H), 3.38 (s, 3H), 2.49 (s, 3H), 1.50 (s, 9H); MS (ES) m/e 223 (M+*H)⁺.

c) Ethyl-6-[(tert-butoxycarbonyl)methylamino]-2-pyridylacetate

LDA was prepared at 0° C. under argon from diisopropylamine (19.5 mL, 139.14 mmole) and 2.5 M n-BuLi in hexanes (46.4 mL, 115.95 mmole) in dry THF (350 mL). This solution was cooled to −78° C. and a solution of 2-[(tert-butoxycarbonyl)methylamino]-6-picoline (10.31 g, 46.38 mmole) in dry THF (46 mL) was added dropwise over 10 min. Additional dry ThF (2 mL) was used in transfer. The orange solution was stirred at −78° C. for 15 min, then diethyl carbonate (6.2 mL, 51.02 mmole) was added rapidly. The red solution was stirred at −78° C. for 15 min, then was quenched with half-saturated NH₄Cl (175 mL). The mixture was warmed to +5° C. and extracted with EtOAc (175 mL) then with CH₂Cl₂ (2×100 mL). The combined organics were washed with brine (100 mL), dried (MgSO₄), and concentrated. The cloudy yellow oil was chromatographed on silica gel (15% EtOAc/hexanes) to afford the title compound (10.72 g. 79%) as a light yellow oil: $^1$H NMR (250 MHz, CDCl₃) δ 7.51–7.63 (m, 2H), 6.91–7.03 (m, 1 H), 4.19 (q, J=7.1 Hz, 2H), 3.77 (s, 2 H), 3.38 (s, 3 H), 1.27 (t, J=7.1 Hz, 3 H), 1.51 (s, 9H); MS (ES) m/e 295 (M+H)⁺.

d) 6-[(tert-Butoxycarbonyl)methylamino]-2-pyridylethanol

A solution of 2 N LiBH₄ in THF (7 mL, 14 mmole) was added via syringe to a stirred solution of ethyl-6-[(tert-butoxycarbonyl)methylamino]-2-pyridylacetate (6.97 g, 23.7 mmole) in anhydrous THF (30 mL) under argon. The reaction was then slowly heated to reflux (initial exotherm). After 16 h at reflux, the reaction was cooled to 0° C. and carefully quenched with water (50 mL). The mixture was extracted with EtOAc (150 mL), and the organic layer was washed with brine, dried (Na₂SO₄), and concentrated. Purification by flash chromatography on silica gel (35% EtOAc/hexane) gave the title compound (5.26 g, 88%) as a clear oil:

$^1$H NMR (400 MHz, CDCl₃) δ 7.57 (m, 2H), 6.88 (d, J=7.2 Hz, 1H), 4.01 (t, 2H), 3.39 (s, 3H), 3.00 (t, 2H), 1.53 (s, 9H); MS (ES) m/e 253.2 (M+H)⁺.

e) 6-(Methylamino)-2-pyridylethanol

To 6-[(tert-butoxycarbonyl)methylamino]-2-pyridylethanol (17.9 g, 71 mmole) was added a solution of 4N HCl in dioxane (200 mL). The reaction was stirred at room temperature for 1 h (gentle gas evolution was observed) then was concentrated to dryness. The product as the hydrochloride salt solidified under vacuum. The solid was dissolved in NaCl-saturated 1.0 N NaOH solution (75 mL), and the solution was extracted with Et₂O (2×200 mL). The combined organic layers were washed with brine, dried (Na₂SO₄), and concentrated to afford the title compound (9.12 g, 85%) as a waxy solid: $^1$H NMR (400 MHz, CDCl₃) δ 7.37 (t, 1 H). 6.42 (d, J=7.3 Hz, 1 H), 6.27 (d, J=8.3 Hz, 1 H), 4.62 (br s, 1H), 3.96 (t, 2H). 2.90 (d, J=5.2 Hz, 3H), 2.84 (t, 2H); MS (ES) m/e 153 (M+H)⁺.

Preparation 2

Preparation of 2-(5,6,7,8-tetrahydro-1,8-naphthyridin-2-yl)-1-ethanol a) 2-(Pivaloylamino)pyridine To a solution of 2-aminopyridine (94.12 g, 1 mole) and Et₃N (167.3 mL, 1.2 mole) in CH₂Cl₂ (1 L) was added pivaloyl chloride (135.5 mL, 1.1 mole) dropwise at 0° C. The mixture was allowed to warm to RT as the bath warmed. After 18 hr the mixture was filtered. The filtrate was washed sequentially with H₂O (1.5 L) and saturated NaHCO₃ (2×1.5 L), then was dried (MgSO₄)and concentrated under reduced pressure to give the title compound (183 g, 103%) as an off-white solid: $^1$H NMR (300 MHz, CDCl₃) δ 8.28 (m, 2H), 8.00 (br s, 1 H), 7.70 (m, 1 H), 7.03 (m, 1 H), 1.31 (s, 9 H); MS (ES) m/e 179 (M+H)⁺.
Note: $^1$H NMR showed the presence of a small amount of tert-butyl containing impurities, but the material is pure enough for use in the next step.

b) 2-(Pivaloylamino)-3-pyridinecarboxaldehyde

To a solution of 2-pivaloylamino)pyridine (17.8 g, 100 mmole) in dry THF (250 mL) at −20° C. was added n-BuLi (2.5 M solution in hexanes, 100 mL, 250 mmoles) dropwise over 30 min. After 2 hr DMF (21 mL, 275 mmoles) was added dropwise over 30 min. The mixture was allowed to warm to RT as the bath warmed. After 18 hr the mixture was quenched with saturated NH₄Cl (300 mL), and the resulting mixture was extracted with EtOAc (3×400 mL). The combined organic layers were dried (MgSO₄) and concentrated to give the title compound as a 2:1 mixture with 2-(pivaloylamino)pyridine (22 g). $^1$H NMR (300 MHz, CDCl₃) δ 10.95 (br s, 1 H), 9.95 (s, 1H), 8.69 (m. 1 H), 8.02 (m, 2 H), 7.20 (m, 1H), 1.38 (s, 9H); MS (ES) m/e 207 (M+H)⁺.
Note: The above procedure was repeated using 1-formylpiperidine (30.5 mL, 275 mmoles) in place of DMF to give the title compound as a 4:1 mixture with 2-(pivaloylamino)pyridine (21 g).

c) 2-Amino-3-pyridinecarboxaldehyde

Crude 2-(pivaloylamino)-3-pyridinecarboxaldehyde (from step b, 43 g) was dissolved in 3 M HCl (500 mL), and the solution was heated to reflux. After 18 hr the mixture was cooled to RT, and the pH was carefully adjusted to 7 using solid K$_2$CO$_3$. The aqueous solution was extracted with EtOAc (3×500 mL). The combined organic layers were dried (MgSO$_4$) and concentrated to give the title compound (24.57 g, 101%) as a reddish brown solid: $^1$H NMR (300 MHz, CDCl$_3$) δ 9.85 (s, 1H), 8.24 (m, 1 H), 7.80 (m, 1H), 6.90 (br s, 2H), 6.74 (m, 2H); MS (ES) m/e 123 (M+H)$^+$.

d) 2-Methyl-1,8-naphthyridine

To a solution of 2-amino-3-pyridinecarboxaldehyde (from step c, 24.57 g) in acetone (750 mL) was added proline (2.3 g, 20 mmole), then the mixture was heated to reflux. After 48 hr the mixture was cooled to RT, filtered, and concentrated. Flash column chromatography on silica gel (35% acetone/hexanes) gave the title compound (18.5 g, 64% over 3 steps) as an orangish-yellow solid: $^1$H NMR (300 MHz, CDCl$_3$) δ 9.07 (m, 1 H), 8.10 (m, 2H), 7.40 (m, 2H), 2.80 (s, 3H); MS (ES) m/e 145 (M+H)$^+$.

e) 2-Methyl-5,6,7,8-tetrahydro-1,8-naphthyridine

A mixture of 2-methyl-1,8-naphthyridine (18.5 g, 128 mmole), 10% Pd/C (5 g), and absolute EtOH (150 mL) was shaken under hydrogen (15 psi) on a Parr apparatus. After 24 hr, the mixture was filtered through celite®, and the filter pad was washed sequentially with absolute EtOH and EtOAc. The filtrate was concentrated to dryness to leave the title compound (18.85 g, 99%) as an off-white solid: $^1$H NMR (300 MHz, CDCl$_3$) δ 7.02 (d, J=7.5 Hz, 1H), 6.34 (d, J=7.5 Hz, 1 H), 4.80 (br s, 1 H), 3.38 (m, 2H), 2.74 (m, 2H), 2.30 (s, 3H), 1.88 (m, 2H); MS (ES) m/e 149 (M+H)$^+$.

f) 2-Methyl-8-(tert-butoxycarbonyl)-5,6,7,8-tetrahydro-1,8-naphthyridine

To a solution of 2-methyl-5,6,7,8-tetrahydro-1,8-naphthyridine (23.32 g, 157 mmole) and di-tert-butyl dicarbonate (44.74 g, 205 mmole) in dry THF (750 mL) at 0° C. was added LiHMDS (1.0 M solution in THF, 205 mL, 205 mmole) dropwise. 30 nin after the addition was complete, the mixture was quenched with saturated NH$_4$Cl (500 mL) and extracted with EtOAc (3×500 mL). The combined organic layers were dried (MgSO$_4$) and concentrated under reduced pressure. Flash column chromatography on silica gel (40% EtOAc/hexanes) gave the title compound (32.3 g, 83%) as a light yellow oil: $^1$H NMR (300 MHz, CDCl$_3$) 57.27 (d. J=7.6 Hz, 1 H), 6.81 (d, J=7.6 Hz, 1 H), 3.69–3.79 (m, 2 H). 2.65–2.75 (m, 2H), 2.48 (s, 3 H), 1.83–1.98 (m. 2 H). 1.52 (s, 9 H): MS (ES) m/e 249 (M+H)$^+$.

g) Ethyl [8-(tert-butoxycarbonyl)-5,6,7,8-tetrahydro-1,8-naphthyridin-2-yl]acetate To a solution of diisopropylamine (47.7 mL, 364 mmole) in dry THF (250 mL) at 0° C. was added n-BuLi (2.5 M in hexanes, 145.6 mL, 364 mmole) dropwise. After 15 min, this solution was added dropwise to a solution of 2-methyl-8-(tert-butoxycarbonyl)-5,6,7,8-tetrahydro-1,8-naphthyridine (32.3 g, 130 mmole) and diethyl carbonate (56.8 mL, 481 mmole) in dry THF (400 mL) at −78° C. After 30 min, the mixture was quenched with saturated NH$_4$Cl (500 mL), warmed to RT, and extracted with EtOAc (3×500 mL). The combined organic extracts were dried (MgSO$_4$), filtered, and concentrated under reduced pressure. Drying under high vacuum overnight gave the title compound (42.52 g, 102%) as a light yellow oil: $^1$H NMR (300 MHz, CDCl$_3$) δ 7.35 (d, J=7.5 Hz, 1 H), 6.96 (d, J=7.5 Hz, 1 H), 4.18 (t, 2H), 3.75 (m, 4 H), 2.72 (t, 2 H), 1.91 (m, 2 H), 1.52 (s, 9 H), 1.24 (m, 3 H); MS (ES) m/e 321 (M+H)$^+$.

Note; $^1$H-NMR showed a small amount of diethyl carbonate present in the product, but the material is pure enough for use in the next step.

h) 2-(5,6,7,8-Tetrahydro-1,8-naphthyridin-2-yl)-1-ethanol

To a solution of ethyl [8-(tert-butoxycarbonyl)-5,6,7,8-tetrahydro-1,8-naphthyridin-2-yl]acetate (42.52 g, 130 mmole) in dry THF (650 mL) at RT was added LiBH$_4$ (2.0 M in THF, 65 mL, 130 mmole), and the resulting mixture was heated to reflux. After 18 hr, the mixture was cooled to 0° C. and carefully quenched with H$_2$O (300 mL). After 10 min, the mixture was extracted with EtOAc (3×500 mL). The combined organic extracts were dried (MgSO$_4$), filtered, and concentrated under reduced pressure.

The above residue was dissolved in CH$_2$Cl$_2$ (300 mL). To this solution was added 4 N HCl in dioxane (300 mL) slowly at RT. After 4 hr the mixture was concentrated under reduced pressure. The residue was taken up in a 1:1 mixture of 1.0 N NaOH and saturated NaCl (300 mL) and extracted with CH$_2$Cl$_2$ (3×300 mL). The combined organic extracts were dried (MgSO$_4$), filtered, and concentrated under reduced pressure. The residue was taken up in Et$_2$O (250 mL) and 96% formic acid (130 mmoles) was added dropwise. The resulting solid was collected by filtration and washed with Et$_2$O (2×50 mL). The solid was dissolved in a 1:1 mixture of 1.0 N NaOH and saturated NaCl (300 mL), and the solution was extracted with CH$_2$Cl$_2$ (3×300 mL). The combined organic extracts were dried (MgSO$_4$), filtered, and concentrated under reduced pressure to give the title compound (11.1 g, 48% over 4 steps) as a yellow solid. $^1$H NMR (300 MHz, CDCl$_3$) δ 7.05 (d, J=7.6 Hz, 1 H), 6.33 (d, J=7.6 Hz, 1 H), 3.90 (t, 2 H), 3.39 (m, 2 H), 2.75 (t, 2 H), 2.70 (t, 2 H), 1.90 (m, 2 H); MS (ES) me 179 (M+H)$^+$.

Preparation 3

Preparation of ethyl (±)-4-(4-hydroxyphenyl)-3-[4-(trifluoromethyl)phenyl]butanoate a) N-Methoxy-N-methyl-2-(4-methoxyphenyl)acetamide

To a solution of 4-methoxyphenylacetic acid (3.3 g, 20 mmole) in dry DMF (75 mL) was added N-methoxy-N-methylamine hydrochloride (1.95 g, 20 mmole), Et$_3$N (3.1 mL, 22 mmole), HOBt H$_2$O (1.95 g, 22 mmole), and EDC (2.7 g, 22 mmole). The solution was stirred at RT overnight, then was concentrated in vacuum. The residue was taken up in 5% Na$_2$CO$_3$ solution (10 mL) and extracted with CH$_2$Cl$_2$ (3×20 mL). The combined organic layers were dried over MgSO$_4$, filtered and concentrated. The residue was chromatographed on silica gel (3% MeOH/CH$_2$Cl$_2$) to give the title compound (1.54 g, 37%) as white solid: MS (ES) m/e 210 (M+H)$^+$.

b) 2-(4-Methoxyphenyl)-1-[4-(trifluoromethyl)phenyl]ethanone

To a solution of sec-BuLi (1.3 M in THF, 22.6 mL, 29.5 mmole) in dry THF (50 mL) was added 4-bromobenzotrifluoride (3.3 g, 14.7 mmole) in dry THF (20 mL) dropwise at −78° C. After 20 min, N-methoxy-N-methyl-2(4-methoxyphenyl)acetamide (1.5 g, 7.4 mmole) in dry THF (20 mL) was added dropwise. After 1 hr the mixture was quenched with saturated NH$_4$Cl (10 mL), warmed to RT, and extracted with Et$_2$O (3×20 mL). The combined organic layers were dried over MgSO$_4$, filtered, and concentrated. The residue was chromatographed on silica gel (15% EtOAc/hexanes) to give the title compound (2.2 g, 100%) as a slightly-yellow solid: TLC (1.5% EtOAc/hexanes) $R_f$ 0.81; $^1$H NMR (300 MHz, CDCl$_3$) δ 8.10 (d, J=8.2 Hz, 2 H), 7.72 (d, J=8.2 Hz, 2 H), 7.18 (d, J=8.7 Hz, 2 H), 6.88 (d, J=8.7 Hz, 2 H), 4.25 (s, 2 H), 3.79 (s, 3 H).

c) Ethyl (±)-4-(4-methoxyphenyl)-3-[4-(trifluoromethyl)phenyl]crotonate

To a suspension of 60% NaH (350 mg, 8.84 mmole) in dry toluene (30 mL) was added triethyl phosphonoacetate (2.0 g, 8.84 mmole) in dry toluene (20 mL) dropwise at RT. After 15 min. a solution of 2-(4-methoxyphenyl)-1-[4-(trifluoromethyl)phenyl]ethanone (1.3 g, 4.42 mmole) in dry toluene (15 mL) was added dropwise, and the solution was heated to reflux. After 16 hr, the reaction was quenched with saturated NH$_4$Cl (10 mL), and the mixture was extracted with EtOAc (3×20 mL). The combined organic layers were dried over MgSO$_4$, filtered, and concentrated. The title compound (2.2 g, 56%, a mixture of two components) was obtained as a light yellow oil: TLC (5% EtOAc/hexanes) $R_f$ 0.42, 0.44. This material was used without further purification.

d) Ethyl (±)-4-(4-methoxyphenyl)-3-[4-(trifluoromethyl)phenyl]butanoate

To a suspension of 10% Pd/C (600 mg) in absolute EtOH (50 mL) was added ethyl (±)-4-(4-methoxyphenyl)-3-[4-(trifluoromethyl)phenyl]crotonate (2.2 g. 6 mmole), and the mixture was shaken on a Parr apparatus at RT under H$_2$ (50 psi). After 4 hr, the mixture was filtered through a pad of celite®, and the filtrate was concentrated. This reaction sequence was repeated three times. The residue was chromatographed on silica gel (35% EtOAc/hexanes) to afford the title compound (900 mg, 56%) as an oil: TLC (5% EtOAc/hexanes) $R_f$ 0.46; $^1$H NMR (300 MHz, CDCl$_3$) δ 7.51 (d, J=8.2 Hz, 2 H), 7.24 (d, J=8.2 Hz, 2 H), 6.94 (d, J=8.7 Hz, 2 H), 6.76 (d, J=8.7 Hz, 2 H), 3.99 (q, J=7.1 Hz, 2 H), 3.76 (s, 3H), 3.35–3.50 (m, 1 H), 2.75–2.93 (m, 2H), 2.69 (dd, J=15.6, 6.4 Hz, 1 H), 2.60 (dd, J=15.6, 8.9 Hz, 1H), 1.11 (t, J=7.1 Hz 3 H).

e) Ethyl (±)-4-(4-hydroxyphenyl)-3-[4-(trifluoromethyl)phenyl]butanoate

To a solution of ethyl (±)-4-(4-methoxyphenyl)-3-[4-(trifluoromethyl)phenyl]butanoate (450 mg, 1.23 mmole) in CH$_2$Cl$_2$ (5 mL) was added BBr$_3$ (1.5 mL, 1.48 mmole) at −10° C. After 3 hr the mixture was carefully quenched with EtOH (10 mL), and the solution was allowed to warm to RT. The mixture was concentrated, and the residue was chromatographed on silica gel (20% EtOAc/hexanes) to give the title compound (270 mg, 63%) as a yellow oil: TLC (20% EtOAc/hexanes) $R_f$ 0.22.

Preparation 4

Preparation of methyl (±)-3-[4-carboxy-1.3-oxazol-2-yl]-4-[(tert-butyloxycarbonyl)oxy]phenyl]butanoate a) 4-Bromo-1-(triisopropylsilyloxy)benzene To a solution of 4-bromophenol (17.3 g, 100 mmole) in dry DMF (100 mL) at RT was added imidazole (13.62 g, 200 mmole), followed by triisopropylsilyl chloride (22.5 mL, 105 mmole). After 4 hr the mixture was diluted with H$_2$O (50 mL) and extracted with hexanes (3×75 mL). The combined organic layers were dried over MgSO$_4$, filtered, and concentrated to give the title compound (32.23 g, 100%) as a clear oil which was used without purification: $^1$H NMR (300 MHz, CDCl$_3$) δ 7.29 (d, J=6 Hz, 2 H), 6.71 (d, J=6 Hz, 2 H), 1.22 (m, 3 H), 1.09 (m, 18 H).

b) Methyl 3-(benzyloxycarbonyl)-3-butenoate

Diisopropyl azodicarboxylate (32.8 mL, 166 mmole) was added to a solution of methyl 3-carboxy-3-butenoate (20 g, 139 mmole), benzyl alcohol (17.2 mg, 166 mmole), and triphenylphosphine (43.7 g. 166 mmole) in anhydrous THF (500 mL) at 0° C. The mixture was allowed to warm as the bath warmed to RT. After 3 hr the mixture was concentrated and the residue was chromatographed on silica gel (10% EtOAc/hexanes).

The title compound (29.46 g, 91%) was obtained as a colorless oil: $^1$H NMR (300 MHz, CDCl$_3$) δ 7.35 (m, 5 H), 6.48 (s, 1 H), 5.71 (s, 1 H), 5.20 (s, 2 H), 3.63 (s, 3 H), 3.37 (s, 2 H).

c) Methyl (±)-4(4-triisopropylsilyloxyphenyl)-3-carboxybutanoate

A solution of 4-bromo-1-(triisopropylsilyloxy)benzene (33.23 g, 100 mmole), methyl 3-(benzyloxycarbonyl)-3-butenoate (28.11 g, 120 mmole), Pd(OAc)$_2$ (2.24 g, 10 mmole), P(o-tolyl)$_3$ (6.09 g, 20 mmole), and (i-Pr)$_2$NEt (34.8 mL, 200 mmole) in propionitrile (350 mL) was deoxygenated (3×evacuation/N$_2$ purge cycles) then was heated to reflux. After 18 hr the mixture was concentrated, and the residue was chromatographed on silica gel (10% EtOAc/hexanes) to give a yellow oil. The oil was taken up in 5% EtOAc/hexanes (100 mL), and the solution was allowed to stand at RT. After 72 hr the mixture was filtered and the filtrate was concentrated to give crude methyl (±)-4-(4-triisopropylsilyloxyphenyl)-3-(benzyloxy-carbonyl)-3-butenoate as a mixture of olefin isomers. This was used immediately in the next step.

The above olefin mixture was divided into two parts. Each part was reacted in the following manner then combined after filtration: To a suspension of 10% Pd/C (7.4 g) in EtOAc (100 mL) was added the above olefin mixture. The mixture was deoxygenated (3×evacuation/N$_2$ purge cycles) then was charged with H$_2$ (50 psi). After 4 hr the H$_2$ was removed and the mixture was filtered through a pad of celite®. The filtrate was concentrated to afford the title compound (24.64 g, 89% from 4-bromo-1-(triisopropylsilyloxy)benzene) as a clear oil: $^1$H NMR (300 MHz, CDCl$_3$) δ 7.01 (d, J=6 Hz, 2 H), 6.80 (d, J=6 Hz, 2 H), 3.62 (s, 3 H), 3.05 (m, 2 H), 2.65 (m, 1 H), 2.40 (m, 2 H), 1.21 (m, 3 H), 1.09 (m, 18 H).

d) (±)-N-[2-[4-(Triisopropylsilyloxy)benzyl]-3-(carbomethoxy)propionyl]serine benzyl ester To a solution of methyl (±)-3-carboxy-4-[4-(triisopropylsilyloxy)phenyl]butanoate (5.00 g, 12.67 mmole) in dry DMF (60 mL) at RT was added serine benzyl ester hydrochloride (3.52 g, 15.21 mmole), HOBt (2.06 g, 15.21 mmole), Et$_3$N (5.3 mL, 38.01 mmole), and EDC (2.92 g, 15.21 mmole). After 18 hr the mixture was concentrated. The residue was chromatographed on silica gel (80% EtOAc/hexanes) to give the title compound (5.76 mg, 79%) as a pale yellow oil: MS (ES) m/e 572 (M+H)$^+$.

e) Methyl (±)-3-[4-benzyloxycarbonyl)-1,3-oxazolin-2-yl]-4-[4-(triisopropylsilyloxy)phenyl]butanoate To a solution of (±)-N-[2-[4-(triisopropylsilyloxy)benzyl]-3-(carbomethoxy)propionyl]serine benzyl ester (5.76 g, 10.07 mmole) in dry THF (50 mL) was added Burgess reagent (2.88 g, 12.08 mmole), then the mixture was heated to reflux. After 2 hr the mixture was cooled to RT and concentrated. The residue was chromatographed on silica gel (35% EtOAc/hexanes) to give the title compound (4.45 g, 80%) as a clear oil: MS (ES) m/e 554 (M+H)$^+$.

f) Methyl (±)-3-[4-(benzyloxycarbonyl)-1,3-oxazol-2-yl]-4-[4-(triisopropylsilyloxy)phenyl]butanoate To a solution of methyl (±)-3-[4-(benzyloxycarbonyl)-1,3-oxazolin-2-yl]-4-[4-(triisopropylsilyloxy)phenyl]butanoate (4.45 g, 8.03 mmole) in CH$_2$Cl$_2$ (40 mL) at 0° C. was added DBU (1.4 mL, 9.64 mmole), followed by bromotrichloromethane (0.95 mL, 9.64 mmole). The mixture was allowed to warm to RT as the bath warmed. After 18 hr the mixture was concentrated. The residue was chromatographed on silica gel (20% EtOAc/hexanes) to give the title compound (2.23 g, 50%) as a clear oil: MS (ES) m/e 552 (M+H)$^+$.

g) Methyl (±)-3-[4-(benzyloxycarbonyl)-1,3-oxazol-2-yl]-4-(4-hydroxyphenyl)butanoate To a solution of methyl (±)-3-[4-(benzyloxycarbonyl)-1,3-oxazol-2-yl]-4-[4-(triisopropylsilyloxy)phenyl]butanoate (2.23 g, 4.04 mmole) in dry THF (20 mL) at 0° C. was added a solution of TBAF in THF (1.0 M, 6.06 mL, 6.06 mmole). After 2 hr the mixture was diluted with saturated NH$_4$Cl (10 mL) and extracted with CH$_2$Cl$_2$ (3×15 mL). The combined organic layers were dried over MgSO$_4$, filtered, and concentrated. The residue was chromatographed on silica gel (40% EtOAc/hexanes) to give the title compound (1.4 g. 88%) as an off-white foam: MS (ES) m/e 396 (M+H)$^+$.

h) Methyl (±)-3-[4-(benzyloxycarbonyl)-1,3-oxazol-2-yl]-4-[4-[(tert-butyloxycarbonyl)oxy]phenyl]butanoate To a solution of methyl (±)-3-[4-(benzyloxycarbonyl)-1,3-oxazol-2-yl]-4-(4-hydroxyphenyl)butanoate (700 mg, 1.77 mmole) and di-tert-butyl dicarbonate (463 mg, 2.12 mmole) in dry THF (10 mL) was added pyridine (0.17 mL, 2.12 mmole) at RT. After 18 hr the mixture was concentrated. The residue was triturated with hexanes, filtered, and dried in vacuo to give the title compound (765 mg, 87%) as a white solid: MS (ES) m/e 496 (M+H)$^+$.

i) Methyl (±)-3-[4-carboxy-1,3-oxazol-2-yl]-4-[4-[(tert-butyloxycarbonyl)oxy]phenyl]butanoate A mixture of methyl (±)-3-[4-(benzyloxycarbonyl)-1,3-oxazol-2-yl]-4-[4-[(tert-butyloxycarbonyl)oxy]phenyl]butanoate (765 mg, 1.54 mmole) and 10% Pd/C (164 mg) in EtOH (20 mL) was deoxygenated (3×evacuation/N$_2$ purge cycles) then was charged with H$_2$ (50 psi). After 4 hr the H$_2$ was removed and the mixture was filtered through a pad of celite®. The filtrate was concentrated to afford the title compound (659 mg, 100%) as a white solid: MS (ES) m/e 811 (2M+H)$^+$.

Preparation 5

Preparation of methyl (±)-3-[4-(trifluoromethyl)thiazol-2-yl]-4-(hydroxyphenyl)butanoate a) 2-Cyanomethyl-4(trifluoromethyl)thiazole 2-Cyanothioacetamide (1.00 g, 9.99 mmole) and 3-bromo-1-trifluoropropan-2-one (1.04 mL. 9.99 mmole) were combined in absolute EtOH (50 mL) and heated to reflux. After 18 hr the mixture was cooled to RT and concentrated. The residue was chromatographed on silica gel (15% EtOAc/hexanes) to give the title compound (1.24 g) as a 2:1 mixture with ethyl 2-cyanoacetate: MS (ES) m/e 385 (2M+H)$^+$.

b) 3-(4-Benzyloxyphenyl)-2-[(trifluoromethyl)thiazol-2-yl]acrylonitrile

NaH (516 mg, 60% dispersion in mineral oil, 12.9 mmole) was reacted with absolute EtOH (10 mL) at 0° C. After gas evolution had ceased the mixture was warmed to RT. 4-Benzyloxybenzaldehyde (2.05 g, 9.68 mmole) was added all at once as a solid. To this mixture was added dropwise a solution of 2-cyanomethyl-4(trifluoromethyl)thiazole (1.24 g) in absolute EtOH (20 mL). The reaction was stirred for 4 hr, then the solid was collected by filtration and washed with hexanes to give the title compound (1.64 g, 42% over 2 steps) as a yellow solid: $^1$H NMR (300 MHz. CDCl$_3$) δ 8.25 (s, 1 H), 8.00 (d, J=6 Hz, 2 H), 7.79(s, 1 H), 7.40 (m, 5 H), 7.10(d, J=6 Hz, 2 H), 5.18 (s, 2 H).

c) 3-(4-Benzyloxyphenyl)-2-cyano-2-[(4-trifluoromethyl)thiazol-2-yl]oxirane

To a solution of 3-(4-enzyloxyphenyl)-2-[(4-trifluoromethyl)thiazol-2-yl]acrylonitrile (500 mg, 1.29 mmole) in CH$_3$CN (5 mL) was added neutral alumina (1.3 g). Clorox bleach (5 mL) was added dropwise at RT. After 1 hr the mixture was filtered. The filtrate was diluted with H$_2$O (20 mL) and extracted with CH$_2$Cl$_2$ (3×20 mL). The combined organic layers were dried over MgSO$_4$, filtered, and concentrated to give the title compound (425 mg, 82%) as a yellow oil which was sufficiently pure for use in the next step. $^1$H NMR (300 MHz, CDCl$_3$) δ 7.90 (s, 1 H), 7.40 (m, 7 H), 7.06 (d, J=6 Hz, 2 H), 5.10 (s, 2 H), 4.59 (s, 1 H).

d) 2-(4-Benzyloxyphenyl)-1-[4-(trifluoromethyl)thiazol-2-yl]ethanone

To a solution of 3-(4-benzyloxyphenyl)-2-cyano-2-[(4-trifluoromethyl)thiazol-2-yl]oxirane (425 mg, 1.06 mmole) in CH$_2$Cl$_2$ (7 mL) was added Et$_3$SiH (0.85 mL, 5.3 mmole) then BF$_3$.OEt$_2$ (0.39 mL, 3.17 mmole) dropwise at 0° C. After 2 hr the mixture was poured into H$_2$O (20 mL) and extracted with CH$_2$Cl$_2$ (3×20 mL). The combined organic layers were dried over MgSO$_4$, filtered, and concentrated.

To the above residue in dry THF (7 mL) was added a solution of TBAF in THF(1.0 M, 1.6 mL, 1.6 mmole) at 0° C. After 1 hr the mixture was poured into saturated NH$_4$Cl (20 mL) and extracted with EtOAc (3×20 mL). The combined organic layers were dried over MgSO$_4$, filtered, and concentrated. The residue was chromatographed on silica gel (5% EtOAc/hexanes) to give the title compound (167 mg, 40%) as a white solid: $^1$H NMR (300 MHz, CDCl$_3$) δ 8.05 (s, 1 H), 7.35 (m, 7 H), 6.92 (d, J=6 Hz, 2 H), 5.05 (s, 2 H), 4.40 (s, 1 H).

e) Methyl (±)-3-[4-(trifluoromethyl)thiazol-2-yl]-4-(4-hydroxyphenyl)butanoate

To a suspension of NaH (35 mg, 0.88 mmole) in dry THF (2 mL) was added triethyl phosphonoacetate (0.17 mL, 0.88 mmole) dropwise at RT. After 15 min, a solution of 2-(4-benzyloxyphenyl)-1-[4(trifluoromethyl)thiazol-2-yl]ethanone (167 mg, 0.44 mmole) in dry THF (2 mL) was added dropwise, and the mixture was heated to reflux. After 18 hr the mixture was cooled to RT, quenched with saturated NH₄C[(10 mL), and extracted with EtOAc (3×20 mL). The combined organic layers were dried over MgSO₄, filtered, and concentrated to afford crude ethyl (±)-3-[4-(trifluoromethyl)thiazol-2-yl]4-(4-benzyloxyphenyl) crotonate as an oil. This was used without purification.

Ethyl (±)-3-[4-(trifluoromethyl)thiazol-2-yl]-4-(4-benzyloxyphenyl)crotonate (0.44 mmole, crude) was dissolved in MeOH (4 mL), and magnesium turnings (53 mg, 2.20 mmole) were added at RT. After 72 hr the mixture was poured into 10% HCl (75 mL) and extracted with CH₂Cl₂ (3×50 mL). The combined organic layers were dried over MgSO₄, filtered, and concentrated to afford crude methyl (±)-3[4-(trifluoromethyl)thiazol-2-yl]-4-benzyloxyphenyl) butanoate. This was used without purification.

To a solution of methyl (±)-3[4-(trifluoromethyl)thiazol-2-yl]-4-(4-benzyloxyphenyl)butanoate (0.44 mmole, crude) in EtSH (5 mL) at RT was added BF₃.OEt₂ (0.3 mL). After 18 hr. additional BF₃.OEt₂ (0.3 mL) was added. After another 18 hr, the mixture was cooled to 0° C. and carefully quenched with saturated NaHCO₃. The resulting mixture was extracted with CH₂Cl₂ (3×25 mL). The combined organic layers were dried over MgSO₄, filtered, and concentrated. The residue was chromatographed on silica gel (30% EtOAc/hexanes) to give the title compound (123 mg, 81% over 3 steps) as a yellow oil: MS (ES) m/e 346 (M+H)⁺.

Preparation 6

Preparation of methyl (±)-3-(5-methylthiazol-2-yl (4-hydroxyphenyl)butanoate a) Methyl 4-(benzyloxy)phenylacetate To a suspension of K₂CO₃ (20.7 g, 150 mmole) in acetone (50 mL) was added methyl 4-hydroxyphenyl acetate (5.0 g, 30 mmole) and benzyl chloride (10.4 mL, 90 mmole) and the mixture was heated to reflux. After 24 hr the mixture was cooled to RT, filtered, and concentrated. The residue was chromatographed on silica gel (10% EtOAc/hexanes) to afford the title compound (7.7 g, 100%) as a white solid: ¹H NMR (300 MHz, CDCl₃) δ 7.40 (m, 5 H), 7.21 (d, J=6.6 Hz, 2 H), 6.95 (d, J=6.6 Hz. 2 H), 5.05 (s, 2 H), 3.70 (s, 3 H), 3.59 (s, 2 H).

b) 2-(4-Benzyloxyphenyl)-1-(5-methylthiazol-2-yl) ethanone

To a solution of 5-methylthiazole (0.21 mL, 2.34 mmole) in dry THF (10 mL) was added n-BuLi (0.94 mL, 2.5 M solution in hexanes, 2.34 mmole) dropwise at −78° C. After 15 min methyl 4-benzyloxyphenyl acetate (0.5 g. 1.95 mmole) in dry THF (5 mL) was added dropwise. After 30 min the mixture was quenched with saturated NH₄Cl (10 mL), warmed to RT, and extracted with EtOAc (3×20 mL). The combined organic layers were dried over MgSO₄, filtered, and concentrated. The residue was chromatographed on silica gel (15% EtOAc/hexanes) to give the title compound as a white solid (532 mg, 51%): MS (ES) m/e 324 (M+H)⁺.

c) Ethyl (±)-4-(4-benzyloxyphenyl)-3-(5-methylthiazol-2-yl)crotonate

To a suspension of NaH (79 mg, 1.98 mmole) in dry THF (2 mL) was added triethyl phosphonoacetate (0.39 mL, 1.98 mmole) dropwise at RT. After 15 min a solution of 2-(4-benzyloxyphenyl)-1-(5-methylthiazol-2-yl)ethanone (320 mg, 0.99 mmole) in dry THF (3 mL) was added dropwise, and the mixture was heated to reflux. After 18 hr the mixture was cooled to RT, quenched with saturated NH₄Cl (10 mL), and extracted with EtOAc (3×20 mL). The combined organic layers were dried over MgSO₄, filtered, and concentrated. The resulting yellow oil was used in the next step without purification: MS (ES) me 394 (M+H)⁺.

d) Methyl (±)-3-(5-methylthiazol-2-yl)-4-(4-benzyloxyphenyl)butanoate

Ethyl (±)-3-(5-methylthiazol-2-yl)-4-(benzyloxyphenyl) crotonate (0.99 mmole, crude) was dissolved in MeOH (5 mL), and magnesium turnings (120 mg, 4.95 mmole) were added at RT. After 72 hr the mixture was poured into 10% HCl (75 mL) and extracted with CH₂Cl₂ (3×50 mL). The combined organic layers were dried over MgSO₄, filtered, and concentrated to afford the crude title compound. This was used without purification: MS (ES) m/e 382 (M+H)⁺.

e) Methyl (±)-3-(5-methylthiazol-2-yl)-4-(4-hydroxyphenyl)butanoate

To a solution of methyl (±)-3-(5-methylthiazol-2-yl)-4-(4-benzyloxyphenyl)butanoate (0.99 mmole, crude) in EtSH (5 mL) at RT was added BF₃ OEt₂ (0.6 mL). After 18 hr. additional BF₃.OEt₂ (0.6 mL) was added. After another 18 hr, the mixture was cooled to 0° C. and carefully quenched with saturated NaHCO₃. The resulting mixture was extracted with CH₂Cl₂ (3×25 mL). The combined organic layers were dried over MgSO₄, filtered, and concentrated. The residue was chromatographed on silica gel (50% EtOAc/hexanes) to give the title compound (249 mg, 86% over 3 steps) as a yellow solid: MS (ES) m/e 292 (M+H)⁺.

Preparation 7

Preparation of (4 R, 5S)-1-acryloyl-3,4-dimethyl-5-phenylimidazolidin-2-one

To a solution of (4 S, 5 R)1,5-dimethyl-4-phenyl-2-imidazolidinone (45.0 g, 237 mmole) and (i-Pr)₂NEt (62 mL, 355 mmole) in CH₂Cl₂ (1200 mL) was added CuCl (50 mg, 0.51 mmole) then acryloyl chloride (29 mL, 355 mmole), and the mixture was heated to reflux. After 2 hr the mixture was cooled to RT, washed with H₂O (3×400 mL), dried over MgSO₄, and concentrated. The resulting solid was triturated with Et₂O (300 mL) and collected by filtration to give the title compound (45.15 g, 78%): ¹H NMR (300 MHz, CDCl₃) δ 7.72 (dd, J=17.0, 10.5 Hz, 1 H), 7.20–7.38 (m, 3 H), 7.10–7.20 (m, 2 H), 6.40 (dd, J=17.0, 2.1 Hz, 1 H), 5.77 (dd, J=10.4, 2.0 Hz, 1 H), 5.36 (d, J=8.5 Hz, 1 H), 3.85–4.00 (m, 1 H), 2.85 (s, 3 H), 0.82 (d, J=6.6 Hz, 3 H); MS (ES) m/e 245 (M+H)⁺.

Preparation 8

Preparation of 4-methoxyphenylmagnesium bromide

A solution of 4-methoxybenzyl chloride (120 g, 766 mmole) in dry THF (1.0 L) was added dropwise over 1.5 hr to a mixture of magnesium turnings (74 g, 3.04 mole) and I₂ (50 mg, 0.20 mmole) in dry THF (0.5 L) at RT. During the initial 10 minutes of addition the brown color dissipated and the reaction became warm. One hour after the addition was complete the reaction returned to RT. Titration using 1,10-phenanthroline indicated the solution was 0.36 M Grignard reagent in THF.

Preparation 9

Preparation of ethyl t(S)-3-(3-fluorophenyl)-4-(4-hydroxyphenyl)butanoate (a) (4 R, 5 S)-3,4-Dimethyl-1-[(E)-3-(3-fluorophenyl)prop-2-enoyl]-5-phenylimidazolidin-2-one A solution of 1-bromo-3-fluorobenzene (525 mg, 3 mmole), (4 R, 5 S)-1-acryloyl-3,4-dimethyl-5- phenylimidazolidin-2-one (500 mg, 2 mmole), Pd(OAc)$_2$ (22 mg, 0.10 mmole), P(o-tolyl)$_3$ (61 mg, 0.20 mmole), and (i-Pr)$_2$NEt (0.73 mL, 4.2 mmole) in dry DMF (10 mL) was degassed (3×vacuum/N$_2$ purge) then heated to 110° C. After 2 hr the mixture was cooled and poured into EtOAc. The resulting mixture was washed with H$_2$O (3×), and the combined aqueous layers were back-extracted with EtOAc. The combined organic layers were dried over MgSO$_4$, filtered through a plug of silica gel, and concentrated. The residue was taken up in 1:1 Et$_2$O/hexanes (10 mL) and cooled at −20° C. overnight. The solid was collected and dried in vacuo to afford the title compound (514 mg, 76%): $^1$H NMR (300 MHz, CDCl$_3$) δ 8.18 (d, J=15.9 Hz, 1 H), 7.64 (d, J=15.9 Hz, 1 H), 7.15–7.45 (m, 8 H), 6.98–7.10 (m, 1 H), 5.42 (d, J=8.5 Hz, 1 H), 3.88–4.03 (m, 1 H), 2.88 (s, 3 H), 0.85 (d, J=6.6 Hz, 3 H); MS (ES) m/e 339 (M+H)$^+$.

(b) (4 R, 5 S)-3,4-Dimethyl-1-[(S)-3-(3-fluorophenyl)-4-(4-methoxyphenyl)butanoyl]-5-phenylimidazolidin-2-one A solution of 4-methoxyphenylmagnesium bromide in THF (0.31 M, 14.7 mL, 4.56 mmole) was added dropwise to a stirred suspension of (4 R, 5 S)-3,4-dimethyl-1-[(E)-3-(3-fluorophenyl)prop-2-enoyl]-5-phenylimidazolidin-2-one (514 mg, 1.52 mmole), CuBr.DMS complex (229 mg, 1.06 mmole), and ZnI$_2$ (582 mg, 1.82 mmole) in THF/toluene (10 mL) at −15° C. After 1.5 hr the reaction was quenched with saturated NH$_4$Cl and extracted with EtOAc (3×). The combined organic layers were dried over MgSO$_4$ and concentrated to dryness. The residue was taken up in 1:1 Et$_2$O/hexanes and cooled at −20° C. for 18 hr. The solid was collected, washed with 1: Et$_2$O/hexanes, and dried in vacuum to afford a first crop of the title compound. The filtrate was concentrated and the residue was purified by flash chromatography on silica gel (30% EtOAc/hexanes) to afford additional title compound as a yellow oil that solidified in vacuum. The total yield of the title compound was 0.62 g(91%): $^1$HNMR (300 MHz, CDCl$_3$) δ 6.75–7.37 (m, 13 H), 5.10 (d, J=8.5 Hz, 1 H), 3.80 (s, 3 H), 3.65–3.85 (m, 1 H), 3.63 (dd, J=16.7, 9.6 Hz, 1 H), 3.36–3.41 (m, 1H), 3.14 (dd, J=16.7, 4.9 Hz, 1 H), 2.72–2.88 (m, 2 H), 2.79 (s, 3 H), 0.74 (d, J=6.6 Hz, 3 H).

(c) Ethyl (S)-3-(3-fluorophenyl)-4-(4-methoxyphenyl)butanoate

A solution of 21% NaOEt in EtOH (0.6 mL, 1.8 mmole) was added to a solution of (4 R, 5 S)-3,4-dimethyl-1-[(S-3-(3-fluorophenyl)-4-(4-methoxyphenyl)butanoyl]-5-phenylimidazolidin-2-one (620 mg, 1.38 mmole) in THF (10 mL). The reaction was stirred for 1 hr, then was quenched with saturated NH$_4$Cl. EtOAc extraction, drying (MgSO4), and concentration left a residue that was filtered through a plug of silica gel (15% EtOAc/hexanes). The filtrate was concentrated to afford the title compound (263 mg, 60%) as a clear oil: $^1$H NMR (300 MHz, CDCl$_3$) δ 7.13–7.35 (m, 1 H), 6.80–7.00 (m, 5 H), 6.70–6.80 (m, 2 H), 4.00 (q, J=7.1 Hz, 2 H), 3.81 (s, 3 H), 3.28–3.45 (m, 1 H), 2.83 (d, J=7.5 Hz, 2 H), 2.65 (dd, J=15.4, 6.4 Hz, 1 H), 2.56 (dd, J=15.4, 8.7 Hz, 1 H), 1.12 (t, J=7.1 Hz, 3H).

(d) Ethyl (S-3-(3-fluorophenyl)-4-(4-hydroxyphenyl)butanoate

To a solution of ethyl (S)-3-(3-fluorophenyl)-4-(4-methoxyphenyl)butanoate (263 mg, 0.83 mmole) in CH$_2$Cl$_2$ (5 mL) at −15° C. was added ethanethiol (0.30 mL. 4.16 mmole) followed by AlCl$_3$ (555 mg, 4.16 mmole). After 30 min, the mixture was warmed to RT, stirred for an additional 30 min, then poured over ice. The ice was allowed to melt, and the mixture was extracted with CH$_2$Cl$_2$ (3×). Drying (MgSO$_4$) and concentration left a residue that was filtered through a plug of silica gel (30% EtOAc/hexanes). Concentration of the filtrate afforded the title compound (250 mg, quantitative): $^1$H NMR (300 MHz, CDCl$_3$) δ 7.10–7.35 (m, 1 H), 6.78–7.00 (m, 5 H), 6.58–6.78 (m, 2 H), 5.00 (s, 1 H), 4.00 (q, 2 H), 3.28–3.45 (m, 1 H), 2.83 (d, 2 H), 2.50–2.75 (m, 2), 1.17 (t, 3H).

Preparation 10

Preparation of ethyl (±)-4-(4-hydroxyphenyl)-3-(pyridin-3-yl)butanoate (a) 2-(tert-Butyldimethylsilyloxy)-2-(pyridin-3-yl)acetonitrile To a solution of 3-pyridinecarboxaldehyde (1.0 g, 9.34 mmole) in CH$_3$CN (45 mL) was added KCN (6.0 g, 93 mmole), TBDMSCl (1.7 g, 11.21 mmole), and ZnI$_2$ (50 mg, 0.16 mmole). After 4 hr at RT the mixture was filtered through celite® and the filtrate was concentrated. Flash chromatography on silica gel (25% EtOAc/hexanes) gave the title compound (2.17 g. 94%) as a clear oil: $^1$H NMR (300 MHz, CDCl$_3$) δ 8.63–8.73 (m, 2 H), 7.80–7.87 (m, 1 H), 7.33–7.41 (m, 1 H), 5.57 (s, 1 H), 0.97 (s, 9 H), 0.27 (s, 3 H), 0.19 (s, 3 H).

(b) (±)-3-(4-Benzyloxyphenyl)-2-(tert-butyldimethylsilyloxy)-2-(pyridin-3-yl)propionitrile LDA was prepared by addition of n-BuLi (2.5 M in hexanes, 1.93 mL, 4.83 mmole) to a solution of diisopropylamine (0.63 mL, 4.83 mmole) in dry THF (5 mL) at 0° C. The LDA solution was added dropwise to a solution of 2-(tert-butyldimethylsilyloxy)-2-(pyridin-3-yl)acetonitrile (1.0 g, 4.03 mmole) in dry THF (15 mL) at −78° C. The solution was stirred for 15 min, then 1 benzyloxybenzyl chloride (1.41 g, 6.05 mmole) was added as a solid all at once. The reaction was kept at −78° C. for 15 min, then was warmed to RT. After 30 min at RT, the reaction was quenched with saturated aqueous NH$_4$Cl and stirred for 20 min. EtOAc extraction (3×), drying (MgSO$_4$), concentration, and flash chromatography on silica gel (20% EtOAc/hexanes) gave the title compound (769 mg, 43%) as a yellow oil: $^1$H NMR (300 MHz, CDCl$_3$) δ 8.80 (narrow m, 1 H), 8.67–8.70 (m, 1 H), 7.75–7.80 (m, 1 H), 7.33–7.53 (m, 6 H), 7.08 (d, 2 H), 6.93 (d, 2 H), 5.10 (s, 2 H), 3.30 (½ Abq, 1 H), 3.18 (½ Abq, 1 H), 0.99 (s, 9 H), 0.12 (s, 3H), 0.08 (s, 3H).

(c) 2-(4-Benzyloxyphenyl)-1-(pyridin-3-yl)ethanone

A solution of TBAF in THF (1.0 M, 2.2 mL, 2.2 mmole) was added dropwise to a solution of (±)-3-(4-benzyloxyphenyl)-2-(ter-butyldimethylsilyloxy)-2-(pyridin-3-yl)propionitrile (769 mg, 1.73 mmole) in dry THF (10 mL) at −15° C. After 30 min, the reaction was partitioned between EtOAc and H$_2$O. The layers were separated and the organic layer was washed with H$_2$O, dried (MgSO$_4$), filtered through a plug of silica gel, and concentrated to afford impure title compound (492 mg, 94%) as a yellow solid: MS (ES) m/e 304 (M+H)$^+$. This material was used without further purification.

(d) Ethyl 4-(4-benzyloxyphenyl)-3-(pyridin-3-yl)but-2-enoate

Triethyl phosphonoacetate (0.70 mL, 3.46 mmole) was added dropwise to a suspension of NaH (60% dispersion in mineral oil, 138 mg, 3.46 mmole) in dry THF (5 mL) at RT. When gas evolution ceased, a solution of 2-(4-benzyloxyphenyl)-1-(pyridin-3-yl)ethanone (ca. 1.73 mmole, impure material from Preparation 10 (c)) in dry THF (5 mL) was added, and the mixture was heated at reflux. After 18 hr, the mixture was cooled to RT, quenched with saturated aqueous NH$_4$Cl, and extracted with EtOAc (3×). The combined organics were dried (MgSO4) and concentrated to afford crude title compound: MS (ES) m/e 374 (M+H)$^+$. This material was used without further purification.

(e) Ethyl (±)-4-(4-hydroxyphenyl)-3-(pyridin-3-yl)butanoate

A mixture of ethyl 4-(4-benzyloxyphenyl)-3-(pyridin-3-yl)but-2-enoate (1.73 mmole) and 10% Pd/C (200 mg) in EtOH (10 mL) was shaken under H$_2$ (50 psi) on a Parr apparatus. After 4 hr, the mixture was filtered through celite®d and the filtrate was concentrated. Flash chromatography on silica gel (50% EtOAc/hexanes) gave the impure title compound (327 mg, 66% over three steps) as a yellow oil: MS (ES) m/e 286 (M+H)$^+$. This material was used without further purification.

Preparation 11

Preparation of ethyl (S)-4-(4-hydroxyphenyl)-3-(pyridin-3-yl)butanoate (a) (4 R, 5 S)-3,4-Dimethyl-1-[(E)-3-(pyridin-3-yl)prop-2-enoyl]-5-phenylimidazolidin-2-one A solution of 3-bromopyridine (8.6 mL, 88.5 mmole), (4 R, 5 S)-1-acryloyl-3,4-dimethyl-5-phenylimidazolidin-2-one (14.4 g. 59 mmole), Pd(OAc)$_2$ (662 mg, 2.95 mmole), P(o-tolyl)$_3$ (1.80 g, 5.9 mmole), and (i-Pr)$_2$NEt (22 mL, 124 mmole) in dry DMF (300 mL) was degassed (3×vacuum/N$_2$ purge) then heated to 110° C. After 2 hr the mixture was cooled and poured into EtOAc. The resulting mixture was washed with H$_2$O (3×), and the combined aqueous layers were back-extracted with EtOAc (2×). The combined organic layers were dried over MgSO$_4$, filtered through a plug of silica gel, and concentrated. The residue was taken up in 1: EtOAc/hexanes and the solid was collected, washed with 1:1 EtOAc/hexanes, and dried in vacuo to afford a first crop of the title compound. The filtrate was concentrated and the crystallization process was repeated to afford a second crop. The total yield of the title compound was 17.53 g (92%): $^1$H NMR (400 MHz, CDCl$_3$) δ 8.48–8.85 (m, 2H), 8.25 (d, J=15.9 Hz, 1 H), 7.89–7.97 (m, 1 H), 7.68 (d, J=15.9 Hz, 1 H), 7.15–7.38 (m, 6 H), 5.43 (d, J=8.5 Hz, 1 H), 3.90–4.02 (m, 1 H), 2.88 (s, 3H), 0.85 (d, J=6.6 Hz, 3 H); MS (ES) m/e 322 (M+H)$^+$.

(b) (4 R, 5 S)-3,4-Dimethyl-1-[(S)-4-(4-methoxyphenyl)-3-(pyridin-3-yl)butanoyl]-5-phenylimidazolidin-2-one A solution of 4-methoxyphenylmagnesium bromide in THF (0.33 M, 495 mL, 163.5 mmole) was added dropwise to a stirred suspension of (4 R, 5 S)-3,4-dimethyl-1-[(E)-3-(pyridin-3-yl)prop-2-enoyl]-5-phenylimidazolidin-2-one (17.53 g, 54.5 mmole), CuBr-DMS complex (14.1 g, 65.4 mmole), and ZnI$_2$ (20.9 g, 65.4 mmole) in THF/toluene (270 mL) at −15° C. After 1 hr the reaction was quenched with 9:1 saturated NH$_4$Cl/conc. NH$_4$OH and the mixture was stirred open to the air for 30 min. The mixture was diluted with H$_2$O and extracted with EtOAc (3×). The combined organic layers were dried over MgSO$_4$ and concentrated. The residue was taken up in methyl tert-butyl ether (MTBE, 200 mL) and stored at −20° C. overnight. The solid was collected, washed with MTBE, and dried in vacuo. This material was recrystallized from 3:1 hexanes/EtOAc to provide the title compound (19.408 g. 80%): $^1$H NMR (400 MHz, CDCl$_3$) δ 8.72 (br s, 2 H), 7.50 (narrow m, 1H), 7.12–7.35 (m, 4 H), 6.97–7.03 (m, 2 H), 6.94 (d, J=8.6 Hz, 2 H), 6.72 (d, J=8.6 Hz, 2H), 5.11 (d, J=8.4 Hz, 1 H), 3.70–3.90(m, 2 H), 3.70 (s, 3 H). 3.43–3.58 (m, 1 H), 3.03–3.18 (m, 1 H), 2.75–2.95 (m, 2 H), 2.71 (s, 3 H), 0.66 (d, J=6.5 Hz, 3 H); MS (ES) m/e 444 (M+H)$^+$.

(c) Ethyl (S)-4-(4-methoxyphenyl)-3-(pyridin-3-yl)butanoate

A solution of 21% NaOEt in EtOH (18.4 mL, 56.88 mmole) was added to a solution of (4 R, 5 S)-3,4-dimethyl-1-[(S)-4-(4-methoxyphenyl)-3-(pyridin-3-yl)butanoyl]-5-phenylimidazolidin-2-one (19.408 g, 43.8 mmole) in THF (200 mL) at 0° C. The reaction was stirred for 1 hr, then was quenched with saturated NH$_4$Cl and extracted with EtOAc (3×). The combined organic layers were dried (MgSO4) and concentrated. The residue was taken up in 1:1 EtOAc/hexanes and filtered, and the filtrate was filtered through a plug of silica gel (1:1 EtOAc/hexanes). The filtrate was concentrated to afford the title compound (9.25 g, 71%) as an orange oil: $^1$H NMR (400 MHz, CDCl$_3$) δ 8.57 (br s, 2 H), 7.44 (narrow m, 1 H), 7.17–7.25 (m, 1 H), 6.95 (d, J=8.6 Hz, 2 H), 6.76 (d, J=8.6 Hz, 2 H), 4.01 (q, J=7.1 Hz. 2 H), 3.75 (s, 3 H), 3.33–3.48 (m, 1 H), 2.91 (dd, J=13.7, 7.3 Hz, 1H), 2.85 (dd, J=13.7, 7.8 Hz, 1 H), 2.71 (dd, J=15.6, 6.5 Hz, 1 H), 2.61 (dd, J=15.6, 8.7 Hz, 1 H), 1.13 (t, J=7.1 Hz, 3 H); MS (ES) m/e 300 (M+H)$^+$.

(d) Ethyl (S)-4-(hydroxyphenyl)-3-(pyridin-3-yl)butanoate

A solution of ethyl (S)-4-(4-methoxyphenyl)-3-(pyridin-3-yl)butanoate (9.25 g, 31 mmole) in CH$_2$Cl$_2$ (150 mL) was cooled to 0° C. Ethanethiol (11.5 mL, 155 mmole) was added, then AlCl$_3$ (20.7 g, 155 mmole) was added portion-wise. After 2 hr, the mixture was poured over ice, allowed to warm to RT, and neutralized with NaHCO$_3$. The resulting suspension was filtered through celite® and the filter pad was washed with CH$_2$Cl$_2$. The layers were separated and the aqueous layer was extracted with CH$_2$Cl$_2$. The combined organic layers were dried (MgSO$_4$) and concentrated. Flash chromatography on silica gel (1:1 EtOAc/hexanes) afforded the title compound (6.435 g, 73%) $^1$H NMR (400 MHz, CDCl$_3$) δ 8.72, 8.41 (dd, J=4.9, 1.5 Hz, 1 H), 8.24 (narrow m, 1 H), 7.26 (dd, J=7.8, 4.9 Hz, 1 H). 6.78 (d, J=8.5 Hz, 2 H), 6.64 (d, J=8.5 Hz, 2 H), 4.03 (q, J=7.1 Hz, 2 H), 3.34–3.48 (m, 1 H), 2.92 (dd, J=13.7, 6.1 Hz, 1 H). 2.69–2.81 (m, 2 H), 2.64 (dd, J=15.6, 8.7 Hz, 1 H), 1.13 (t, J=7.1 Hz, 3 H); MS (ES) m/e 286 (M+H)$^+$.

EXAMPLE 1

Preparation of (±)-4-[4-[2-[6-(methylamino)pyridin-2-yl-1-ethoxy]phenyl]-3-[4-(trifluoromethyl)phenyl]butanoic acid a) Ethyl (i)-4-[4-[2-[6-(methylamino)pyridin-2-yl]-1-ethoxy]phenyl]-3-[4-(trifluoromethyl)phenyl]butanoate Diisopropyl azodicarboxylate (0.15 mL, 0.767 mmole) was added over 2 min to a solution of ethyl (±)-4-(4-hydroxyphenyl)-3-[4(trifluoromethyl)phenyl]butanoate (270 mg, 0.767 mmole), 6-(methylamino)-2-pyridylethanol (130 mg, 0.92 mmole), and triphenylphosphine (200 mg, 0.767 mmole) in anhydrous THF (5 mL) at 0° C. under $N_2$. The yellow solution was kept at 0° C. for 10 min, then was warmed to RT. After 24 hr. the reaction was concentrated and the residue was chromatographed on silica gel (20 EtOAc/hexanes). The title compound (200 mg, 54%) was obtained as a colorless oil: MS (ES) m/e 487 (M+H)$^+$.

b) (±)-4-[4-[2-[6-(Methylamino)pyridin-2-yl]-1-ethoxy]phenyl]-3-[4-(trifluoromethyl)phenyl]butanoic acid 1.0 N NaOH (8.2 mL, 0.823 mmole) was added dropwise to a cooled (15° C.) solution of ethyl (±)-4-[4-[2-[6-(methylamino)pyridin-2-yl]-1 ethoxy]phenyl]-3-[4-(trifluoromethyl)phenyl)butanoate (200 mg, 0.41 mmole) in MeOH (3 mL), and the mixture was stirred at RT for 24 hr. The resulting solution was concentrated in vacuum and the residue was dissolved in $H_2O$ (5 mL). The pH was adjusted to 5 with 1.0 N HCl, and the precipitate was collected, washed with small amount of water, and dried in vacuum at 60° C. The title compound (120 mg, 64%) was obtained as a white, foamy solid: MS (ES) me 459 (M+H)$^+$. Anal. Calcd for $C_{25}H_{25}FN_2O_3 \cdot 0.85H_2O$: C, 63.38; H, 5.68; N, 5.91. Found: C, 63.23; H, 5.41; N, 5.73.

EXAMPLE 2

Preparation of (±)-4-[4-[2-[6(methylamino)pyridin-2-yl]-1-ethoxy]phenyl]-3-[4-[(N-methyl-N-phenylamino)carbonyl]1,3-oxazol-2-yl]-butanoic acid a) Methyl (±)-3-[4-[(N-methyl-N-phenylamino)carbonyl]-1,3-oxazol-2-yl]-4-(4-hydroxyphenyl)butanoate To a solution of methyl (±)-3-[4-carboxy-1,3-oxazol-2-yl]-4-[4-[(tert-butyloxycarbonyl)oxy]phenyl]butanoate (150 mg, 0.37 mmole), (i-Pr)$_2$NEt (0.1 mL, 0.56 mmole), pyridine (0.09 mL, 1.11 mmole), and N-methylaniline (0.06 mL, 0.56 mmole) in dry DMF (2 mL) was added BPFFH (382 mg, 1.11 mmole) at RT. After 18 hr the mixture was concentrated. The residue was taken up in 10% HCl (20 mL) and extracted with $CH_2Cl_2$ (3×20 mL). The combined organic layers were dried over $MgSO_4$, filtered, and concentrated.

The above residue was dissolved in 4 N HCl in dioxane (10 mL) at RT. After 18 hr the mixture was concentrated. The residue was chromatographed on silica gel (75% EtOAc/hexanes) to give the title compound (146 mg) as an orange foam contaminated with bis(pentamethylene)urea: MS (ES) m/e 417 (M+H)$^+$.

b) Methyl (±)-4-[4-[2-(6-methylaminopyridin-2-yl)-1-ethoxy]phenyl]-3-[4-[(N-methyl-N-phenylamino)carbonyl]-1,3-oxazol-2-yl)]butanoate Diisopropyl azodicarboxylate (0.15 ml, 0.74 mmole) was added to a solution of methyl (±)-3-[4-(N-methyl-N-phenylamino)carbonyl]-1,3-oxazol-2-yl]-4-(4-hydroxyphenyl)butanoate (146 mg, 0.37 mmole), 6-(methylamino)-2-pyridylethanol (113 mg, 0.74 mmole), and triphenylphosphine (194 mg, 0.74 mmole) in $CH_2Cl_2$ (2 mL) at 0° C. The mixture was allowed to warm to RT as the bath warmed. After 18 hr the mixture was concentrated and the residue was chromatographed on silica gel (50% THF/hexanes). Fractions containing the product were concentrated to give the title compound (322 mg) contaminated with triphenylphosphine oxide: MS (ES) m/e 529 (M+H)$^+$.

c) (i)-4-[4-[2-[6-(Methylamino)pyridin-2-yl]-ethoxy]phenyl]-3-[4-[(N-phenyl-N-methylamino)carbonyl]-1,3-oxazol-2-yl]-butanoic acid To a solution of methyl (±)-4-[4-[2-(6-methylaminopyridin-2-yl)-1-ethoxy]phenyl]-3-[4-[(N-methyl-N-phenylamino)carbonyl]-1,3-oxazol-2-yl)] butanoate (322 mg) in 1:1 THF/$H_2O$ (2 mL) at RT was added 1.0 N LiOH (0.35 mL, 0.35 mmole). After 18 hr the mixture was acidified to pH 6 using 10% HCl then was concentrated to dryness. The residue was purified by reverse-phase HPLC (gradient: 10–80% $CH_3CN/H_2O$ containing 0.1% TFA). The fractions containing the product were combined and concentrated to remove $CH_3CN$. The resulting aqueous solution was lyophilized to give the title compound (33 mg, 29% over 3 steps) as a white solid: MS (ES) m/e 515 (M+H)$^+$. Anal. Calcd for $C_{29}H_3N_4O_5 \cdot 1.85$ TFA: C, 54.13; H, 4.42; N, 7.72. Found: C, 54.17; H, 4.50; N, 7.52.

EXAMPLE 3

Preparation of (±)-4-[4-[2-[6(methylamino)pyridin-2-yl]-1-ethoxy]phenyl]-3-[4-(morpholin-4-yl)carbonyl]-1,3-oxazol-2-yl]-butanoic acid a) Methyl (±)-3-[4-(morpholin-4-yl)carbonyl]-1,3-oxazol-2-yl]-4-hydroxyphenyl)butanoate To a solution of methyl (±)-3-[4-carboxy-1,3-oxazol-2-yl]-4-[4-[(tert-butyloxycarbonyl)oxy]phenyl]butanoate (150 mg, 0.37 mmole), (i-Pr)$_2$NEt (0.1 mL, 0.56 mmole), pyridine (0.09 mL, 1.11 mmole), and morpholine (0.05 mL, 0.56 mmole) in dry DMF (2 mL) was added BPFFH (382 mg, 1.11 mmole) at RT. After 18 hr the mixture was concentrated. The residue was taken up in 10% HCl (20 mL) and extracted with $CH_2Cl_2$ (3×20 mL). The combined organic layers were dried over $MgSO_4$, filtered, and concentrated.

The above residue was dissolved in 4 N HCl in dioxane (10 mL) at RT. After 18 hr the mixture was concentrated. The residue was chromatographed on silica gel (100% EtOAc) to give the title compound (122 mg, 88%) as a clear oil: $^1$H NMR (300 MHz, CDCl$_3$) δ 8.05 (s, 1H), 7.88 (d, J=6.6 Hz, 2H), 6.70 (d, J=6.6 Hz, 2H), 5.9 (s, 1H), 3.73 (bs, 8 H), 3.62 (s, 3 H), 2.85 (m, 5H).

b) Methyl (±)-4-[4-[2-(6-methylaminopyridin-2-yl)-1-ethoxy]phenyl]-3-[4-(morpholin-4-yl)carbonyl]-1,3-oxazol-2-yl)]butanoate Diisopropyl azodicarboxylate (0.13 mL, 0.66 mmole) was added to a solution of methyl (±)-3-[4-(morpholin-4-yl)carbonyl]-1,3-oxazol-2-yl]-4-(4-hydroxyphenyl)butanoate (122 mg, 0.37 mmole), 6-(methylamino)-2-pyridylethanol (100 mg, 0.66 mmole), and triphenylphosphine (173 mg. 0.66 mmole) in $CH_2Cl_2$ (2 mL) at 0° C. The mixture was allowed to warm to RT as the bath warmed. After 18 hr the mixture was concentrated and the residue was chromatographed on silica gel (100% EtOAc). Fractions containing the product were concentrated to give the title compound (94 mg) contaminated with triphenylphosphine oxide. MS (ES) m/e 509 (M+H)$^+$.

c) (±)-4-[4-[2-[6-(Methylamino)pyridin-2-yl]-1-ethoxy]phenyl]-3-[4(morpholin-4-yl)carbonyl]-1,3-oxazol-2-yl]-butanoic acid To a solution of methyl (±)-4-[4-[2-(6-methylaminopyridin-2-yl)-1-ethoxy]phenyl]-3-[4-

(morpholin-4-yl)carbonyl]-1,3-oxazol-2-yl)]butanoate (94 mg, 0.18 mmole) in 1:1 THF/H$_2$O (2 mL) at RT was added 1.0 N LiOH (0.25 mL, 0.25 mmole). After 18 hr the mixture was acidified to pH 6 using 10% HCl then was concentrated to dryness. The residue was purified by reverse-phase HPLC (gradient; 15–35% CH$_3$CN/H$_2$O containing 0.1% TFA). The fractions containing the product were combined and concentrated to remove CH$_3$CN. The resulting aqueous solution was lyophilized to give the title compound (23 mg, 26% over 2 steps) as a white solid: MS (ES) m/e 495 (M+H)$^+$. Anal. Calcd for C$_{26}$H$_{30}$N$_4$O$_6$.1.75 TFA: C, 49.76; H, 4.78; N, 7.87. Found: C, 49.93; H, 4.97; N, 7.84.

EXAMPLE 4

Preparation of (±)-4-[4-[2-[6(methylamino pyridin-2-yl]-1-ethoxy]phenyl]-3-[4-[[N-methyl-N-(2,2,2-trifluoroethyl)amino]carbonyl]-1,3-oxazol-2-yl]-butanoic acid a) Methyl (±)-3-[4-[[N-methyl-N-(2,2,2-trifluoroethyl)amino]carbonyl]-1,3-oxazol-2-yl]-4-(4-hydroxyphenyl)butanoate To a solution of methyl (±)-3-[4-carboxy-1,3-oxazol-2-yl]-4-[4-[(tert-butyloxycarbonyl)oxy]phenyl]butanoate (150 mg, 0.37 mmole), (i-Pr)$_2$NEt (0.1 mL, 0.56 mmole), pyridine (0.09 mL, 1.11 mmole), and N-methyl-N-(2,2,2-trifluoroethyl)amine hydrochloride (84 mg, 0.56 mmole) in dry DMF (2 mL) was added BPFFH (382 mg, 1.11 mmole) at RT. After 18 hr the mixture was concentrated. The residue was taken up in 10% HCl (20 mL) and extracted with CH$_2$Cl$_2$ (3×20 mL). The combined organic layers were dried over MgSO$_4$, filtered, and concentrated.

The above residue was dissolved in 4 N HCl in dioxane (10 mL) at RT. After 18 hr the mixture was concentrated. The residue was chromatographed on silica gel (60% EtOAc/hexanes) to give the title compound (298 mg) as a clear oil contaminated with bis(pentamethylene)urea. The oil was used in the next step without further purification.

b) Methyl (±)-4-[4-[2-(6-methylaminopyridin-2-yl)-1-ethoxy]phenyl]-3-[4-[[N-methyl-N(2,2,2-trifluoroethyl)amino]carbonyl]-1,3-oxazol-2-yl)]butanoate Diisopropyl azodicarboxylate (0.15 mL, 0.74 mmole) was added to a solution of methyl (±)-3-[4-[[N-methyl-N-(2,2,2-trifluoroethyl)amino]carbonyl]-1,3-oxazol-2-yl]-4-(4-hydroxyphenyl)butanoate (298 mg, 0.37 mmole), 6-(methylamino)-2-pyridylethanol (113 mg, 0.74 mmole), and triphenylphosphine (194 mg. 0.74 mmole) in CH$_2$Cl$_2$ (2 mL) at 0° C. The mixture was allowed to warm to RT as the bath warmed. After 18 hr the mixture was concentrated and the residue was chromatographed on silica gel (40% EtOAc/hexanes). Fractions containing the product were concentrated to give the title compound (115 mg) contaminated with triphenylphosphine oxide: MS (ES) m/e 535 (M+H)$^+$.

c) (±)-4-[4-[2-[6-(Methylamino)pyridin-2-yl]-1-ethoxy]phenyl]-3-[4-[[N-methyl-N-(2,2,2-trifluoroethyl)amino]carbonyl]-1,3-oxazol-2-yl]-butanoic acid To a solution of methyl (±)-4-[4-[2-(6-methylaminopyridin-2-yl-1-ethoxy]phenyl]-3-[4-[[N-methyl-N-(2,2,2-trifluoroethyl)amino]carbonyl]-1,3-oxazol-2-yl)]butanoate (115 mg, 0.22 mmole) in 1:1 THF/H$_2$O (2 mL) at RT was added 1.0 N LiOH (0.32 mL, 0.32 mmole). After 18 hr the mixture was acidified to pH 6 using 10% HCl then was concentrated to dryness. The residue was purified by reverse-phase HPLC (gradient: 10–80% CH$_3$CN/H$_2$O containing 0.1% TFA). The fractions containing the product were combined and concentrated to remove CH$_3$CN. The resulting aqueous solution was lyophilized to give the title compound (42 mg, 37% over 3 steps) as a white solid: MS (ES) m/e 522 (M+H)$^+$. Anal. Calcd for C$_{25}$H$_{27}$F$_3$N$_4$O$_5$.1.4 TFA: C, 49.09; H, 4.21 N, 8.24. Found: C, 49.18; H, 4.18; N, 8.22.

EXAMPLE 5

Preparation of (±)-4-[4-[2-(6-(methylaminopyridin-2-yl]-1-1-ethoxy]phenyl]-3-4-(trifluoromethyl)thiazol-2-yl]butanoic acid a) Methyl (±)-4-[4-[2-(6-methylaminopyridin-2-yl)-1-ethoxy]phenyl]-3-[4-(trifluoromethyl)thiazol-2-yl]butanoate Diisopropyl azodicarboxylate (0.14 mL, 0.71 mmole) was added to a solution of methyl (±)-3-[4(trifluoromethyl)thiazol-2-yl]-4-hydroxyphenyl)butanoate (123 mg, 0.37 mmole), 6-(methylamino)-2-pyridylethanol (108 mg, 0.71 mmole), and triphenylphosphine (186 mg, 0.71 mmole) in CH$_2$Cl$_2$ (2 mL) at 0° C. The mixture was allowed to warm to RT as the bath warmed. After 18 hr the mixture was concentrated and the residue was chromatographed on silica gel (40% EtOAc in 1:1 toluene/hexanes). Fractions containing the product were concentrated to give the title compound (114 mg, contaminated with reduced DIAD): MS (ES) m/e 480 (M+t)$^+$.

b) (±)-4-[4-[2-[6-(Methylamino)pyridin-2-yl]-1-ethoxy]phenyl]-3-[4-(trifluoromethyl)thiazol-2-yl]-butanoic acid To a solution of methyl (±)-4-[4-[2-(6-methylaminopyridin-2-yl-1-ethoxy]phenyl]-3-[4-(trifluoromethyl)thiazol-2-yl-butanoate (114 mg, 0.24 mmole) in 1:1 THF/H$_2$O (2 mL) at RT was added 1.0 N LiOH (0.36 mL, 0.36 mmole). After 18 hr the mixture was acidified to pH 6 using 10% HCl. The resulting solid was collected by filtration and dried in vacuo at 50° C. to give the title compound (43 mg, 42%) as a white solid: MS (ES) m/e 466 (M+H)$^+$. Anal. Calcd for C$_{22}$H$_{22}$F$_3$N$_3$O$_3$S.0.2H$_2$O: C, 56.33; H, 4.81; N. 8.96. Found: C, 56.34; H. 4.69; N, 8.88.

EXAMPLE 6

Preparation of (±)-4-[4-[2-(6-methylaminopyridin-2-yl)-1-ethoxy]phenyl]-3-(5-methylthiazol-2-yl)butanoic acid a) Methyl(±)-4-[4-[2-(6-Methylaminopyridin-2-yl)-1-ethoxy]phenyl]-3-(5-methylthiazol2-yl)butanoate Diisopropyl azodicarboxylate (0.25 mL, 1.28 mmole) was added to a suspension of methyl (±)-4-(4-hydroxyphenyl)-3-(5-methylthiazol-2-yl)butanoate (249 mg, 0.85 mmole), 6-(methylamino)-2-pyridylethanol (194 mg, 1.28 mmole), and triphenylphosphine (336 mg, 1.28 mmole) in TBME (5 mL) at 0° C. The mixture was allowed to warm to RT as the bath warmed. After 72 hr the mixture was concentrated and the residue was chromatographed on silica gel (30% EtOAc/CHCl$_3$). Fractions containing the product were concentrated to give the title compound (385 mg, contaminated with triphenylphosphine oxide): MS (ES) m/e 426 (M+H)$^+$.

b) (±)-[4-[4-[2-(6-Methylaminopyridin-2-yl)-1-ethoxy]phenyl]-3-(5-methylthiazol-2-yl) butanoic acid To a solution of methyl (±)-[4-[4-[2-(6-methylaminopyridin-2-yl)-1-ethoxy]phenyl]-3-(5-methylthiazol-2-yl)butanoate (0.85 mmole) in 1:1 THF/H$_2$O (5 mL) was added 1.0 N NaOH (1.28 mL, 1.28 mmole). After 18 hr the mixture was acidified to pH 6 using 10% HCl then concentrated to dryness. The residue was chromatographed on silica gel (EtOH) to give the title compound as a yellow solid (217 mg, 62% over 2 steps). MS (ES) m/e 412 (M+H)$^+$. Anal. Calcd for C$_{22}$H$_{25}$N$_3$O$_3$S 1.2H$_2$O: C, 61.01; H. 6.38; N. 9.70. Found: C, 61.25; H. 6.06; N, 9.32.

EXAMPLE 7

Preparation of (S-3-(3-fluorophenyl)-4-[4-[2-(5,6,7,8-tetrahydro-1,8-naphthyridin-2-yl)ethoxy]phenyl] butanoic acid (a) Ethyl (S)-3-(3-fluorophenyl)-4-[4-[2-(5,6,7,8-tetrahydro-1,8-naphthyridin-2-yl)ethoxy]phenyl] butanoate Diisopropyl azodicarboxylate (0.20 mL, 1.0 mmole) was added dropwise to a solution of ethyl (S)-3-(3-fluorophenyl)-4-(4-hydroxyphenyl)butanoate (250 mg, 0.83 mmole), 2-(5,6,7,8-tetrahydro-1,8-naphthyridin-2-yl)-1-ethanol (178 mg, 1.0 mmole), and triphenylphosphine (262 mg, 1.0 mmole) in anhydrous THF (5 mL) at RT. After 18 hr the reaction was concentrated and the residue was flash chromatographed on silica gel (5:1 Et$_2$O/hexanes) to afford impure title compound (236 mg, 61%): MS (ES) m/e 463 (M+H)$^+$. This was used without further purification.

(b) (S)-3-(3-Fluorophenyl)-4-[2-(5,6,7,8-tetrahydro-1,8-naphthyridin-2-yl)ethoxy]phenyl]butanoic acid 1.0 N LiOH (0.76 mL, 0.76 mmole) was added to a solution of ethyl (S)-3-(3-fluorophenyl)-4-[4-[2-(5,6,7,8-tetrahydro-1,8-naphthyridin-2-yl)ethoxy]phenyl]butanoate (236 mg, 0.51 mmole) in THF/H$_2$O (3 mL), and the mixture was heated at 50° C. After 18 hr the mixture was cooled to RT and acidified to pH 6 with 10% aqueous HCl. EtOAc (5 mL) was added and the mixture was stirred vigorously. The solid was collected by suction filtration, washed with H$_2$O (2×) and Et$_2$O (2×), and dried in vacuo at 50° C. to afford the title compound; MS (ES) m/e 435 (M+H)$^+$. Anal. Calcd for C$_{26}$H$_{27}$FN$_2$O$_3$.2.25 HCl: C, 60.46; H. 5.71; N, 5.42. Found: C, 60.44; H. 5.34; N. 5.45.

EXAMPLE 8

Preparation of (±)-4-[4-[2-[6-(methylamino)pyridin-2-yl]ethoxy]phenyl]-3-(pyridin-3-yl)butanoic acid (a) Ethyl (±)-4-[4-[2-[6-(methylamino)pyridin-2-yl]ethoxy]phenyl]-3-(pyridin-3-yl)butanoate According to the procedure of Example 7 (a), except substituting ethyl 4-(4-hydroxyphenyl)-3-(pyridin-3-yl)butanoate (327 mg impure, 1.15 mmole) for the ethyl (S)-3-(3-fluorophenyl)-4-(4-hydroxyphenyl)butanoate, and substituting 6-(methylamino)-2-pyridylethanol (210 mg, 1.38 mmole) for the 2-(5,6,7,8-tetrahydro-1,8-naphthyridin-2-yl)1-ethanol, the title compound was prepared as an impure, light orange solid following flash chromatography on silica gel (100% EtOAc): MS (ES) m/e 420 (M+H)$^+$. This material was used without further purification.

(b) (±)-4-[4-[2-[6-(Methylamino)pyridin-2-yl]ethoxy]phenyl]-3-(pyridin-3-yl)butanoic acid 1.0 N LiOH (3.45 mL, 3.45 mmole) was added to a solution of ethyl (±)-4-[4-2-[6-(methylamino)pyridin-2-yl]ethoxy]phenyl]-3-(pyridin-3-yl)butanoate (1.15 mmole) in THF/H$_2$O (5 mL), and the mixture was heated at 50° C. After 18 hr the reaction was cooled to RT and acidified to pH 6 with 10% aqueous HCl. The mixture was extracted with CHCl$_3$ (3×), and the combined organic layers were dried (MgSO$_4$) and concentrated. The residue was chromatographed on a C-18 Bond-Elute column (20% CH$_3$CN/H$_2$O). The fractions containing the product were pooled and extracted with CHCl$_3$ (3×), and the combined organic layers were dried (MgSO$_4$) and concentrated. The resulting solid was taken up in 2 M NaOH and washed with EtOAc (2×). The EtOAc extracts were discarded. The aqueous layer was acidified to pH 6 and extracted with CHCl$_3$ (3×). The combined organic layers were dried (MgSO$_4$) and concentrated to afford the title compound (51 mg, 11%) as a white solid: $^1$H NMR (300 MHz, CDCl$_3$) δ 8.32 (m, 2 H), 7.54 (dd, J=8.7, 7.2, Hz, 1H), 7.38–7.46 (m, 1 H), 7.12 (dd, 1=7.8, 4.9 Hz, 1 H), 6.86 (d, J=8.6 Hz, 2 H), 6.68 (d, J=8.6 Hz, 2 H), 6.52 (d, J=7.2 Hz, 1 H), 6.37 (d, J=8.7 Hz, 1 H), 4.15–4.30 (m, 2 H), 3.39–3.52 (m, 1 H), 2.98–3.20 (m, 3 H), 2.85 (s, 3 H), 2.80 (dd, J=13.7, 8.9 Hz, 1 H), 2.68 (dd, J=15.1, 8.3 Hz, 1 H), 2.59 (dd, J=15.1, 6.7 Hz, 1 H); MS (ES) m/e 392 (M+H)$^+$. Anal. Calcd for C$_{23}$H$_{25}$N$_3$O$_3$.1.3 HCl: C, 62.95; H, 6.04; N, 9.57. Found: C, 62.84; H, 5.87; N, 9.20.

EXAMPLE 9

Preparation of (S)-4-[4-[2-6-(methylamino)pyridin-2-yl]ethoxy]phenyl]-3-(pyridin-3-yl)butanoic acid (a) Ethyl (S)-4-[4-[2-[6-(methylamino)pyridin-2-yl]ethoxy]phenyl]-3-(pyridin-3-yl)butanoate Diisopropyl azodicarboxylate (7.8 mL, 39.8 mmole) was added dropwise to a solution of ethyl (S)-4-(4-hydroxyphenyl)-3-(pyridin-3-yl)butanoate (9.455 g, 33.1 mmole), 6-(methylamino)-2-pyridylethanol (6.06 g, 39.8 mmole), and triphenylphosphine (10.44 g, 39.8 mmole) in anhydrous THF (150 mL) at 0° C. The mixture was allowed to warm to RT as the bath warmed. After 18 hr the reaction was concentrated and the residue was flash chromatographed on silica gel (3% MeOH in 1:1 EtOAc/CHCl$_3$) to afford the title compound (9.2 g, 66%) as a viscous yellow oil: $^1$H NMR (400 MHz, CDCl$_3$) δ 8.43 (dd, J=4.8, 1.6 Hz, 1 H). 8.39 (d, J=1.9 Hz, 1 H), 7.31–7.45 (m, 2 H), 7.13–7.21 (m, 1 H), 6.91 (d, J=8.6 Hz, 2 H), 6.77 (d, 3=8.6 Hz, 2 H), 6.53 (d, J=7.3 Hz, 1 H), 6.24 (d, J=8.2 Hz, 1 H), 4.43–4.58 (m, 1 H), 4.26 (t, J=7.0 Hz, 2 H), 3.92–4.05 (m, 2 H), 3.32–3.45 (m, 1 H), 3.04 (t, J=7.0 Hz, 2 H), 2.89 (d, J=5.3 Hz, 3 H), 2.88 (dd, J=13.7, 7.2 Hz, 1 H), 2.82 (dd, J=13.7, 7.8 Hz, 1 H), 2.70 (dd, J=15.6, 6.3 Hz, 1 H), 2.59 (dd, J=15.6, 9.0 Hz, 1 H), 1.11 (t, J=7.1 Hz, 3 H); MS (ES) m/e 420 (M+H)$^+$.

(b) (S)-4-[4-[2-[6-(Methylamino)pyridin-2-yl]ethoxy]phenyl]-3-(pyridin-3-yl)butanoic acid 2.0 M NaOH (15 mL, 30 mmole) was added to a solution of ethyl (S)-4-[4-[2-[6-(methylamino)pyridin-2-yl]ethoxy]phenyl]-3-(pyridin-3-yl)butanoate (9.2 g, 22 mmole) in dioxane/H$_2$O (100 mL), and the mixture was heated at 50° C. After 18 hr, the reaction was cooled to RT, acidified with 10% HCl (25 mL), and concentrated to 1/3 volume to precipitate a gum. The supernatant was decanted and the gum was partitioned between $H_2O$ and $CHCl_3$. The layers were separated and the aqueous layer was extracted with $CHCl_3$ (3×). The combined organic layers were dried ($MgSO_4$) and concentrated, and the residue was taken up in $H_2O$ and 2 M NaOH (30 mL). The solution was washed with $Et_2O$ (3×), and the $Et_2O$ extracts were discarded. The aqueous solution was acidified with 10% HCl (50 mL), concentrated to 1/3 volume, and extracted with $CHCl_3$ (3×). The organic layers were combined, dried ($MgSO_4$), and concentrated to leave a foam. This foam was taken up in $CH_2Cl_2$, and the solution was diluted with hexanes and concentrated. This process was repeated three times. The resulting solid was dried in vacuo at 65° C. to afford the title compound (7.96 g, 92%): $^1H$ NMR (400 MHz, MeOH-$d_4$) δ 88.28 (narrow m, 1 H), 8.21 (d, J=1.7 Hz, 1 H), 7.68 (narrow m, 1 H), 7.48 (dd, J=8.5, 7.3 Hz, 1 H), 7.30 (dd, J=7.9, 4.9 Hz, 1 H), 6.91 (d, J=8.6 Hz, 2 H), 6.72 (d, J=8.6 Hz, 2 H), 6.56 (d, J=7.3 Hz, 1 H), 6.44 (d, J=8.5 Hz, 1 H), 4.20 (t, J=6.6 Hz, 2 H), 3.31–3.42 (m, 1 H), 3.02 (t, J=6.6 Hz, 2 H), 2.97 (dd, J=13.6, 6.5 Hz, 1 H), 2.87 (s, 3 H), 2.77 (dd, J=13.6, 8.9 Hz, 1 H), 2.71 (dd, J=15.6, 6.4 Hz, 1 H), 2.62 (dd, J=15.6, 8.9 Hz, 1 H); MS (ES) m/e 392 (M+H)$^+$. Anal. Calcd for $C_{23}H_{25}N_3O_3 \cdot 0.1H_2O$: C, 70.25; H, 6.46; N, 10.68. Found: C, 70.32; H, 6.50; N, 10.32.

EXAMPLE 10

Preparation of (S)-3-(pyridin-3-yl)-4-[4-[2-(5,6,7,8-tetrahydro-1,8-naphthyridin-2-yl)ethoxy]phenyl]butanoic acid (a) Ethyl (S)-3-(pyridin-3-yl)-4-[4-[2-(5,6,7,8-tetrahydro-1,8-naphthyridin-2-yl)ethoxy]phenyl]butanoate Diisopropyl azodicarboxylate (0.41 mL, 2.1 mmole) was added dropwise to a solution of ethyl (S)-4-(4-hydroxyphenyl)-3-pyridin-3-yl)butanoate (500 mg, 1.75 mmole), 2-(5,6,7,8-tetrahydro-1,8-naphthyridin-2-yl)-1-ethanol (374 mg, 2.1 mmole), and triphenylphosphine (551 mg, 2.1 mmole) in anhydrous THF (8 mL) at RT. After 18 hr the reaction was concentrated and the residue was flash chromatographed on silica gel (90% EtOAc/hexanes then 5% EtOH/EtOAc) to afford the title compound (572 mg, 73%) as an oil: $^1H$ NMR (400 MHz, CDCl$_3$) δ 8.43 (dd, J=4.8, 1.6 Hz, 1 H), 8.39 (d, J=1.9 Hz, 1 H), 7.41 (narrow m, 1 H), 7.17 (dd, J=7.8, 4.8 Hz, 1 H), 7.07 (d, j=7.3 Hz, 1 H), 6.90 (d, J=8.6 Hz, 2 H), 6.76 (d, =8.6 Hz, 2 H), 6.44 (d, J=7.3 Hz, 1 H), 4.75 (br s, 1 H), 4.21 (t, J=7.0 Hz, 2 H), 3.93–4.08(m, 2 H), 3.31–3.45(m, 3 H), 2.99(t, J=7.0 Hz, 2 H), 2.88 (dd, J=13.7, 7.2 Hz, 1 H), 2.82 (dd, J=13.7, 7.8 Hz, 1 H), 2.65–2.75 (m, 3 H), 2.59 (dd, J=15.6, 9.0 Hz, 1 H). 1.85–1.95 (m, 2 H), 1.12 (t, J=7.1 Hz, 3 H); MS (ES) m/e 446 (M+H)$^+$.

(b) (S)$_3$-(Pyridin-3-yl)-4-[4-[2-(5,6,7,8-tetrahydro-1,8-naphthyridin-2-yl)ethoxy]phenyl]butanoic acid 1.0 M LiOH (2.6 mL, 2.6 mmole) was added to a solution of ethyl (S)-3-(pyridin-3-yl)-4-[4-[2-(5,6,7,8-tetrahydro-1,8-naphthyridin-2-yl)ethoxy]phenyl]butanoate (572 mg, 1.28 mmole) in THF/H$_2$O (8 mL), and the mixture was heated at 50° C. After 18 hr, the reaction was cooled to RT and acidified to pH 6.0 with 10% HCl. The precipitated solid was collected by suction filtration, washed with $H_2O$, and dried in vacuo to afford the title compound (414 mg, 77%): $^1H$ NMR (400 MHz, MeOH-d$_4$) δ 8.28 (dd, J=4.9, 1.4 Hz, 1 H), 8.21 (d, J=1.8 Hz, 1 H). 7.68 (d, J=8.0 Hz, 1 H), 7.25–7.27 (m, 2 H), 6.91 (d, I=8.6 Hz, 2 H), 6.71 (d, J=8.6 Hz, 2 H), 6.53 (d, J=7.3 Hz, 1 H), 4.08–4.22 (m, 2 H), 3.30–3.45 (m, 3 H), 2.90–3.05 (m, 3 H), 2.70–2.85 (m, 3 H), 2.68 (dd, J=15.2, 6.7 Hz, 1 H), 2.58 (dd, J=15.2, 8.5 Hz, 1 H), 1.80–1.97 (m, 2 H); MS (ES) m/e 418 (M+H)$^+$. Anal. Calcd for $C_{23}H_{25}N_3O_3 \cdot 0.25H_2O$: C, 71.15; H, 6.57; N, 9.96. Found: C, 71.11; H, 6.66; N, 9.82.

EXAMPLE 11

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

EXAMPLE 12

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

EXAMPLE 13

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I):

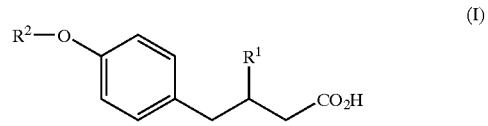

wherein:

$R^1$ is

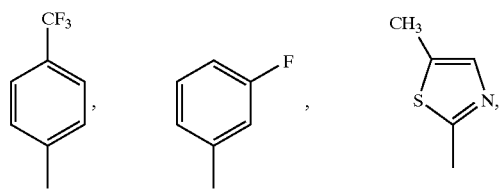

51

-continued

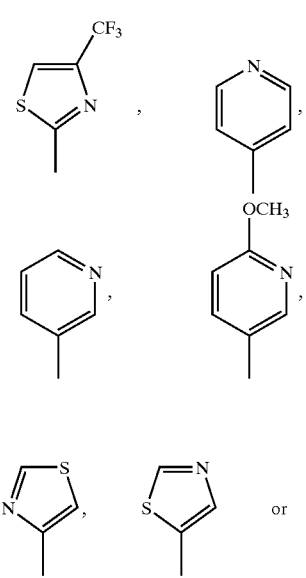

in which R' is C$_{1-4}$alkyl and R" is phenyl, benzyl or —CH$_2$CF$_3$; or R' and R" are joined to form a morpholinyl ring;

R$^2$ is

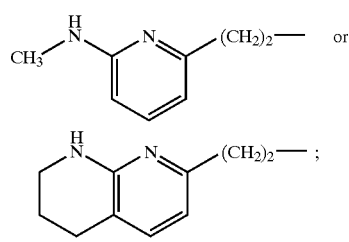

or a pharmaceutically acceptable salt thereof.

2. A compound according to claim 1 in which R$^2$ is:

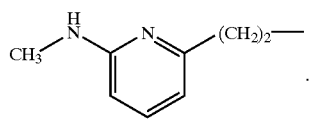

3. A compound according to claim 1 in which R$^2$ is:

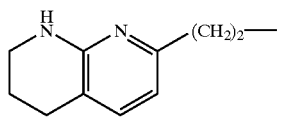

4. A compound which is:
(±)-4-[4-[2-[6-(methylamino)pyridin-2-yl]-1-ethoxy]phenyl]-3-[4-(trifluoromethyl)phenyl]butanoic acid;
(±)-4-[4-[2-[6-(methylamino)pyridin-2-yl]-1-ethoxy]phenyl]-3-[4-[(N-methyl-N-phenylamino)carbonyl]-1,3-oxazol-2-yl]butanoic acid;
(±)-4-[4-[2-[6-(methylamino)pyridin-2-yl]-1-ethoxy]phenyl]-3-[4[(morpholin-4-yl)carbonyl]-1,3-oxazol-2-yl]butanoic acid;
(±)-4-[4-[2-[6-(methylamino)pyridin-2-yl]-1-ethoxy]phenyl]-3-[4-[[N-methyl-N-(2,2,2-trifluoroethyl)amino]carbonyl]-1,3-oxazol-2-yl]butanoic acid;
(±)-4-[4-[2-[6-(methylamino)pyridin-2-yl]-1-ethoxy]phenyl]-3-[4-(trifluoromethyl)thiazol-2-yl]butanoic acid;
(±)-4-[4-[2-[6-(methylamino)pyridin-2-yl]-1-ethoxy]phenyl]-3-(3-methylthiazol-2-yl)butanoic acid;
(S)-3-(3-fluorophenyl)-4-[4-[2-(5,6,7,8-tetrahydro-1,8-naphthyridin-2-yl)ethoxy]phenyl]butanoic acid;
(±)-4-[4-[2-[6-(methylamino)pyridin-2-yl]ethoxy]phenyl]-3-(pyridin-3-yl)butanoic acid;
(S)-4-[4-[2-[6-(methylamino)pyridin-2-yl]ethoxy]phenyl]-3-(pyridin-3-yl) butanoic acid; or
(S)-3-(pyridin-3-yl)-4-[4-[2-(5,6,7,8-tetrahydro-1,8-naphthyridin-2-yl)ethoxy]phenyl]butanoic acid;
or a pharmaceutically acceptable salt thereof.

5. A pharmaceutical composition which comprises a compound according to claim 1 and a pharmaceutically acceptable carrier.

6. A method of treating osteoporosis which comprises administering to a subject in need thereof a therapeutically effective amount of a compound according to claim 1.

* * * * *